(12) United States Patent
Hauser et al.

(10) Patent No.: US 11,865,218 B2
(45) Date of Patent: Jan. 9, 2024

(54) TARGETED APPROACH FOR ULTRAVIOLET DISINFECTION OF SURFACES

(71) Applicant: The Board of Trustees of the University of Illinois, Urbana, IL (US)

(72) Inventors: Kristoffer Karl Hauser, Bloomington, IN (US); Joao Marcos Correia Marques, Urbana, IL (US); Zherong Pan, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 685 days.

(21) Appl. No.: 17/085,416

(22) Filed: Oct. 30, 2020

(65) Prior Publication Data

US 2022/0088237 A1    Mar. 24, 2022

Related U.S. Application Data

(60) Provisional application No. 63/082,410, filed on Sep. 23, 2020.

(51) Int. Cl.
*G06N 20/00* (2019.01)
*A61L 2/10* (2006.01)

(52) U.S. Cl.
CPC ............... *A61L 2/10* (2013.01); *G06N 20/00* (2019.01); *A61L 2202/11* (2013.01);
(Continued)

(58) Field of Classification Search
CPC .... A61L 2/10; A61L 2202/11; A61L 2202/14; A61L 2202/16; A61L 2202/20; G06N 20/00

See application file for complete search history.

(56) References Cited

U.S. PATENT DOCUMENTS 6,656,424 B1 * 12/2003 Deal ................... A61L 2/28
                                                       250/455.11
7,251,853 B2    8/2007 Park et al.
(Continued)

OTHER PUBLICATIONS

K. Bedell, A. H. Buchaklian, and S. Perlman, "Efficacy of an automated multiple emitter whole-room ultraviolet-c disinfection system against coronaviruses mhv and mers-cov," infection control & hospital epidemiology, vol. 37, No. 5, pp. 598-599, 2016.
(Continued)

*Primary Examiner* — Gary Collins
(74) *Attorney, Agent, or Firm* — McDonnell Boehnen Hulbert & Berghoff LLP

(57) ABSTRACT

An embodiment may involve obtaining a three-dimensional image map of m surfaces within an environment, wherein the surfaces are associated with importance weights that represent how frequently the surfaces are expected to be touched; determining a set of n vantage points for a light source within the environment; calculating an m×n irradiance matrix for each of the surfaces when the light source is in each of the vantage points, wherein each entry in the m×n irradiance matrix is determined by: (i) rasterizing the three-dimensional image map, (ii) identifying a set of visible surfaces, and (iii) calculating an amount of light-based power that would reach each of the visible surfaces; determining a set of n dwell times for the vantage points; and providing instructions, to a disinfecting agent, to traverse at least a subset of the vantage points, pausing at and illuminating at least some.

20 Claims, 14 Drawing Sheets

(52) U.S. Cl.
CPC ....... *A61L 2202/14* (2013.01); *A61L 2202/16* (2013.01); *A61L 2202/20* (2013.01)

(56) References Cited

U.S. PATENT DOCUMENTS

| | | | | |
|---|---|---|---|---|
| 8,067,750 | B2* | 11/2011 | Deal | A61L 2/10 422/1 |
| 2008/0260601 | A1 | 10/2008 | Lyon | |
| 2017/0112954 | A1* | 4/2017 | Dayton | A61L 9/20 |
| 2021/0299868 | A1* | 9/2021 | Vitzrabin | A61L 2/24 |
| 2021/0346541 | A1* | 11/2021 | Callahan | A61L 2/10 |

OTHER PUBLICATIONS

D. Armellino, K. Goldstein, L. Thomas, T. J. Walsh, and V. Petraitis, "Comparative evaluation of operating room terminal cleaning by two methods: Focused multivector ultraviolet (fmuv) versus manual-chemical disinfection," American Journal of Infection Control, vol. 48, No. 2, pp. 147-152, 2020.

D. Mackenzie, "Ultraviolet light fights new virus," Engineering (Beijing, China), 2020.

E. Galceran, R. Campos, N. Palomeras, D. Ribas, M. Carreras, and P. Ridao, "Coverage path planning with real-time replanning and surface reconstruction for inspection of three-dimensional underwater structures using autonomous underwater vehicles," Journal of Field Robotics, vol. 32, No. 7, pp. 952-983, 2015.

A. Bircher, M. Kamel, K. Alexis, M. Burri, P. Oettershagen, S. Omari, T. Mantel, and R. Siegwart, "Threedimensional coverage path planning via viewpoint resampling and tour optimization for aerial robots," Autonomous Robots, vol. 40, No. 6, pp. 1059-1078, 2016.

G. Papadopoulos, H. Kurniawati, and N. M. Patrikalakis, "Asymptotically optimal inspection planning using systems with differential constraints," in 2013 IEEE International Conference on Robotics and Automation, IEEE, 2013, pp. 4126-4133.

A. Bircher, K. Alexis, U. Schwesinger, S. Omari, M. Burri, and R. Siegwart, "An incremental samplingbased approach to inspection planning: The rapidly exploring random tree of trees," Robotica, vol. 35, No. 6, pp. 1327-1340, 2017.

M. Fu, A. Kuntz, O. Salzman, and R. Alterovitz, "Toward asymptotically-optimal inspection planning via efficient near-optimal graph search," arXiv preprint arXiv:1907.00506, 2019.

G. Bahr, J. Kereiakes, H Horwitz, R Finney, J Galvin, and K Goode, "The method of linear programming applied to radiation treatment planning," Radiology, vol. 91, No. 4, pp. 686-693, 1968.

E. K. Lee, T. Fox, and I. Crocker, "Integer programming applied to intensity-modulated radiation therapy treatment planning," Annals of Operations Research, vol. 119, No. 1-4, pp. 165-181, 2003.

G. A. Ezzell, "Genetic and geometric optimization of three-dimensional radiation therapy treatment planning," Medical Physics, vol. 23, No. 3, pp. 293-305, 1996.

S. Sumikura, M. Shibuya, and K. Sakurada, "OpenVSLAM: A Versatile Visual SLAM Framework," in Proceedings of the 27th ACM International Conference on Multimedia, ser. MM '19, Nice, France: ACM, 2019, pp. 2292-2295.

J. C. Mosher, R. M. Leahy, and P. S. Lewis, "Eeg and meg: Forward solutions for inverse methods," IEEE Transactions on Biomedical Engineering, vol. 46, No. 3, pp. 245-259, 1999.

M. F. Cohen and D. P. Greenberg, "The hemi-cube: A radiosity solution for complex environments," ACM Siggraph Computer Graphics, vol. 19, No. 3, pp. 31-40, 1985.

G. Coombe, M. J. Harris, and A. Lastra, "Radiosity on graphics hardware," in Proceedings of Graphics Interface 2004, Citeseer, 2004, pp. 161-168.

S. Green, "The openGL framebuffer object extension," in Game developers conference, vol. 2005, 2005.

Bailey, Mike. "OpenGL Compute Shaders." Oregon State University (2016).

Harris, Mark, Shubhabrata Sengupta, and John D. Owens. "Parallel prefix sum (scan) with CUDA." GPU gems 3, No. 39 (2007): 851-876.

E. Heitz, J. Dupuy, S. Hill, and D. Neubelt, "Realtime polygonal-light shading with linearly transformed cosines," ACM Transactions on Graphics (TOG), vol. 35, No. 4, pp. 1-8, 2016.

L. L. C. Gurobi Optimization, Gurobi Optimizer Reference Manual, 2018.

K. Helsgaun, "Effective implementation of the Lin-Kernighan traveling salesman heuristic," European Journal of Operational Research, vol. 126, No. 1, pp. 106-130, Oct. 2000.

M. Saha, G. S'anchez-Ante, and J.-C. Latombe, "Planning multi-goal tours for robot arms," in 2003 IEEE International Conference on Robotics and Automation (Cat. No. 03CH37422), IEEE, vol. 3, 2003, pp. 3797-3803.

S. Edelkamp, M. Pomarlan, and E. Plaku, "Multiregion inspection by combining clustered traveling salesman tours with sampling-based motion planning," IEEE Robotics and Automation Letters, vol. 2, No. 2, pp. 428-435, 2016.

R. Geraerts and M. H. Overmars, "Clearance based path optimization for motion planning," in IEEE International Conference on Robotics and Automation, 2004. Proceedings. ICRA'04. 2004, IEEE, vol. 3, 2004, pp. 2386-2392.

M. Heßling, K. H¨ones, P. Vatter, and C. Lingenfelder, "Ultraviolet irradiation doses for coronavirus inactivation—review and analysis of coronavirus photoinactivation studies.," GMS hygiene and infection control, vol. 15, Doc08, 2020.

A. N. Letchford, S. D. Nasiri, and D. O. Theis, "Compact formulations of the steiner traveling salesman problem and related problems," European Journal of Operational Research, vol. 228, No. 1, pp. 83-92, 2013.

* cited by examiner

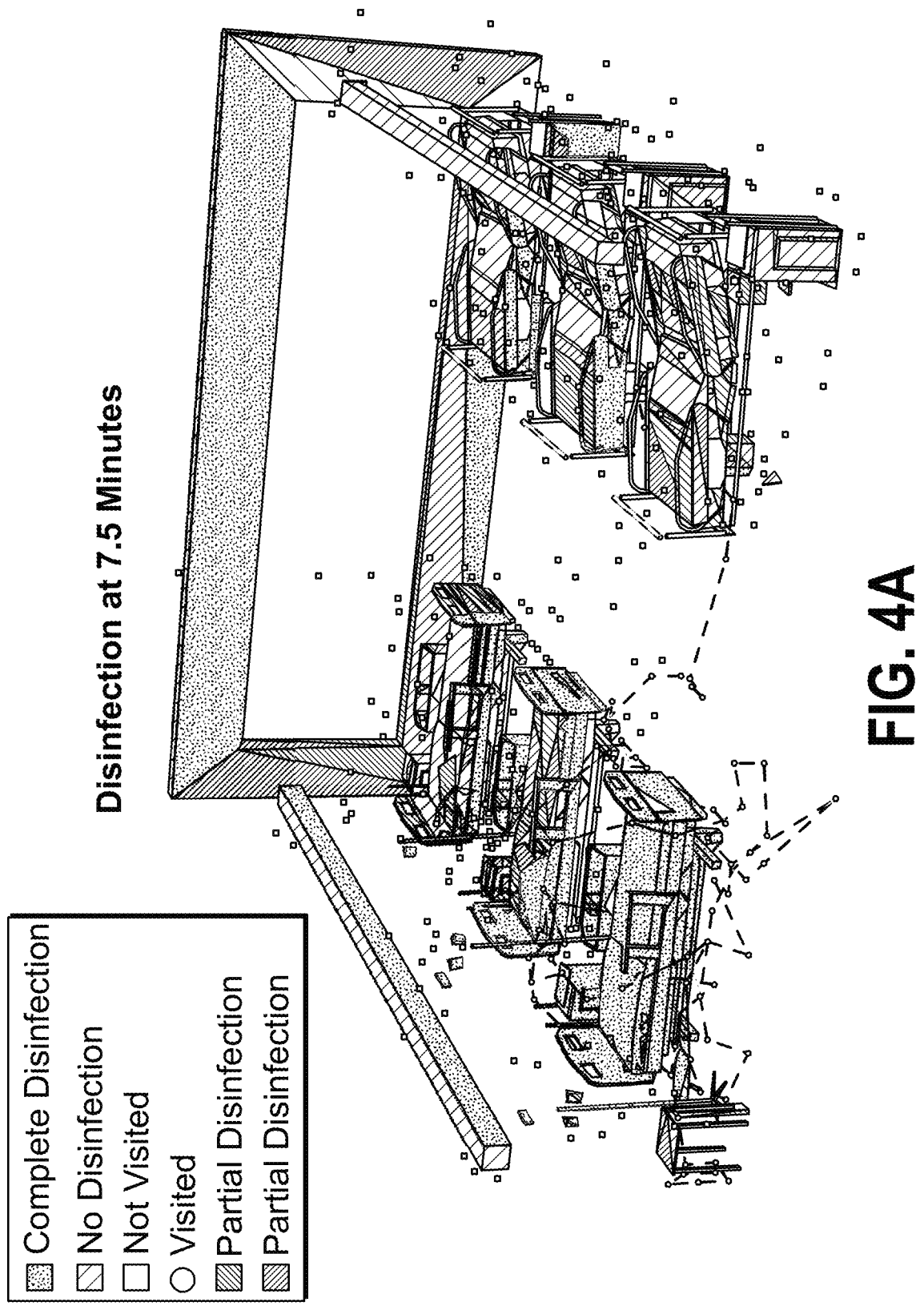

TARGETED APPROACH FOR ULTRAVIOLET DISINFECTION OF SURFACES

CROSS-REFERENCE TO RELATED APPLICATION

This application claims priority to U.S. provisional patent application No. 63/082,410, filed Sep. 23, 2020, which is hereby incorporated by reference in its entirety.

BACKGROUND

The Coronavirus pandemic has encouraged worldwide innovation in methods for reducing the risk of disease transmission in hospitals, transportation, places of business, and public spaces. One promising technology under investigation is ultraviolet (UV) disinfection of surfaces, which has strong antimicrobial properties particularly in the UVC (200 nm to 280 nm) spectrum. UV deactivates a wide range of pathogens including Coronavirus, Middle East Respiratory Syndrome (MERS), etc., and a combination of standard manual cleaning followed by UVC irradiation has shown to be more effective than manual cleaning alone.

Existing approaches to deliver UV irradiation include air and water disinfection systems, as well as surface disinfection systems in the form of wands, overhead lights, pushcarts, and mobile robots carrying high-power UVC lamps. Dosing is an important factor in applying UVC effectively, and is usually performed by following manufacturers' guidelines. Although some UV disinfection robots also feature sensors that measure reflected radiant energy as an approximation of surface dosage, these coarse methods fail to target the dosage to the geometry of the target surfaces. Disinfection efficiency for a given surface is proportional to radiant fluence (radiant exposure), which drops off sharply with increasing distance (due to the inverse square law), the angle of incidence of light rays, and in the presence of occlusions.

Moreover, disinfection effort should be focused on high-touch surfaces because they are more likely to receive microbes pre-disinfection and pass them on post-disinfection. These drawbacks of stationary and/or fixed orientation UV lamps have been recognized by others and form the basis of devices that use actuators to reorient lamps toward surfaces and around obstacles.

SUMMARY

The embodiments herein present a technique for measurement, visualization, and targeted dosage optimization for UV disinfection of irregular surfaces. The technique is comprised of: 1) three-dimensional mapping using a camera and/or laser sensors, 2) visibility detection and irradiance calculation using graphics processing units (GPUs), and 3) optimization of the dosing strategy to achieve a targeted level of disinfection fluence, which may vary depending on the microbe under consideration and whether a surface is high-touch, low-touch, or irrelevant. For example, walls are low-touch and should receive a lower disinfection fluence, whereas high-touch surfaces like handles, bedrails, and IV stands are of high importance and should be irradiated with higher priority.

The surface classification can be provided by manual annotation or via automated machine learning algorithms that are trained to identify surfaces by appearance and/or spatial position. The technique also provides for visual feedback of disinfection quality to an operator or supervisor, in the form of a three-dimensional model where quantities of interest, such as radiant fluence, irradiance, or estimated viral load, are color-coded as a heatmap. The resulting dosing strategies can be implemented by a disinfecting agent. The disinfection agent could be in a controllable mobile light positioning mechanism, such as an automated mobile robot or mobile manipulator, or a human operator. The method may also be implemented to provide feedback to coach a human operator using a disinfection wand or push cart.

The technical contributions of this work include fast GPU-based irradiance determination of surfaces from arbitrary vantage points, vantage point distribution strategies that account for reachability of the light positioning mechanism, dosage optimization using numerical optimization (linear programming, or LP) techniques, and traversal strategy optimization using a Traveling Salesman Problem (TSP) solver. Experiments compare this approach to the status quo of UV disinfection mobile robots that stay in one spot, and show that the method is able to disinfect empty rooms 65% faster. Moreover, in models of cluttered hospital rooms, the technique is able to achieve 100% coverage in the same time that the status quo only achieves 30% coverage.

Also presented is a "gold standard" method for jointly encoding the LP+TSP problem as a Mixed-Integer Linear Program (MILP) to obtain optimal solutions. The MILP is intractable to solve for realistic problems, but serves as a reference point to compare the efficiency of the proposed LP+TSP technique. Experiments in simple environments suggest that the two stage approach only sacrifices 2-5% of disinfection time compared to the gold standard while remaining orders of magnitude faster in solving the optimization.

Accordingly, a first example embodiment may involve (i) obtaining a three-dimensional image map of m surfaces within an environment, wherein the surfaces are respectively associated with importance weights, and wherein the importance weights represent how frequently the surfaces are expected to be touched; (ii) determining a set of n vantage points for a light source within the environment; (iii) calculating an m×n irradiance matrix representing irradiance presented to each of the surfaces when the light source is in each of the vantage points, wherein each entry in the m×n irradiance matrix is determined by: (1) rasterizing the three-dimensional image map for a given candidate vantage point, (2) identifying a set of visible surfaces from the three-dimensional image map as rasterized, and (3) calculating an amount of light-based power that would reach each of the visible surfaces; (iv) determining a set of n dwell times, one associated with each of the vantage points, using linear programming over the m×n irradiance matrix, the importance weights, and an overall time constraint; and (v) providing instructions, to a disinfecting agent, to traverse at least a subset of the vantage points, pausing at each in accordance with the associated dwell times and illuminating at least some of the surfaces while paused.

In a second example embodiment, an article of manufacture may include a non-transitory computer-readable medium, having stored thereon program instructions that, upon execution by a computing system, cause the computing system to perform operations in accordance with the first example embodiment.

In a third example embodiment, a computing system may include at least one processor, as well as memory and program instructions. The program instructions may be stored in the memory, and upon execution by the at least one processor, cause the computing system to perform operations in accordance with the first example embodiment.

In a fourth example embodiment, a system may include various means for carrying out each of the operations of the first example embodiment.

These, as well as other embodiments, aspects, advantages, and alternatives, will become apparent to those of ordinary skill in the art by reading the following detailed description, with reference where appropriate to the accompanying drawings. Further, this summary and other descriptions and figures provided herein are intended to illustrate embodiments by way of example only and, as such, that numerous variations are possible. For instance, structural elements and process steps can be rearranged, combined, distributed, eliminated, or otherwise changed, while remaining within the scope of the embodiments as claimed.

BRIEF DESCRIPTION OF THE DRAWINGS

FIGS. 4A, 4B, 4C, and 4D illustrate different disinfection times of a hospital room, in accordance with example embodiments.

DETAILED DESCRIPTION

Example methods, devices, and systems are described herein. It should be understood that the words "example" and "exemplary" are used herein to mean "serving as an example, instance, or illustration." Any embodiment or feature described herein as being an "example" or "exemplary" is not necessarily to be construed as preferred or advantageous over other embodiments or features unless stated as such. Thus, other embodiments can be utilized and other changes can be made without departing from the scope of the subject matter presented herein.

Accordingly, the example embodiments described herein are not meant to be limiting. It will be readily understood that the aspects of the present disclosure, as generally described herein, and illustrated in the figures, can be arranged, substituted, combined, separated, and designed in a wide variety of different configurations. For example, the separation of features into "client" and "server" components may occur in a number of ways.

Further, unless context suggests otherwise, the features illustrated in each of the figures may be used in combination with one another. Thus, the figures should be generally viewed as component aspects of one or more overall embodiments, with the understanding that not all illustrated features are necessary for each embodiment.

Additionally, any enumeration of elements, blocks, or steps in this specification or the claims is for purposes of clarity. Thus, such enumeration should not be interpreted to require or imply that these elements, blocks, or steps adhere to a particular arrangement or are carried out in a particular order.

I. Example Computing Devices and Cloud-Based Computing Environments

Figure 1:
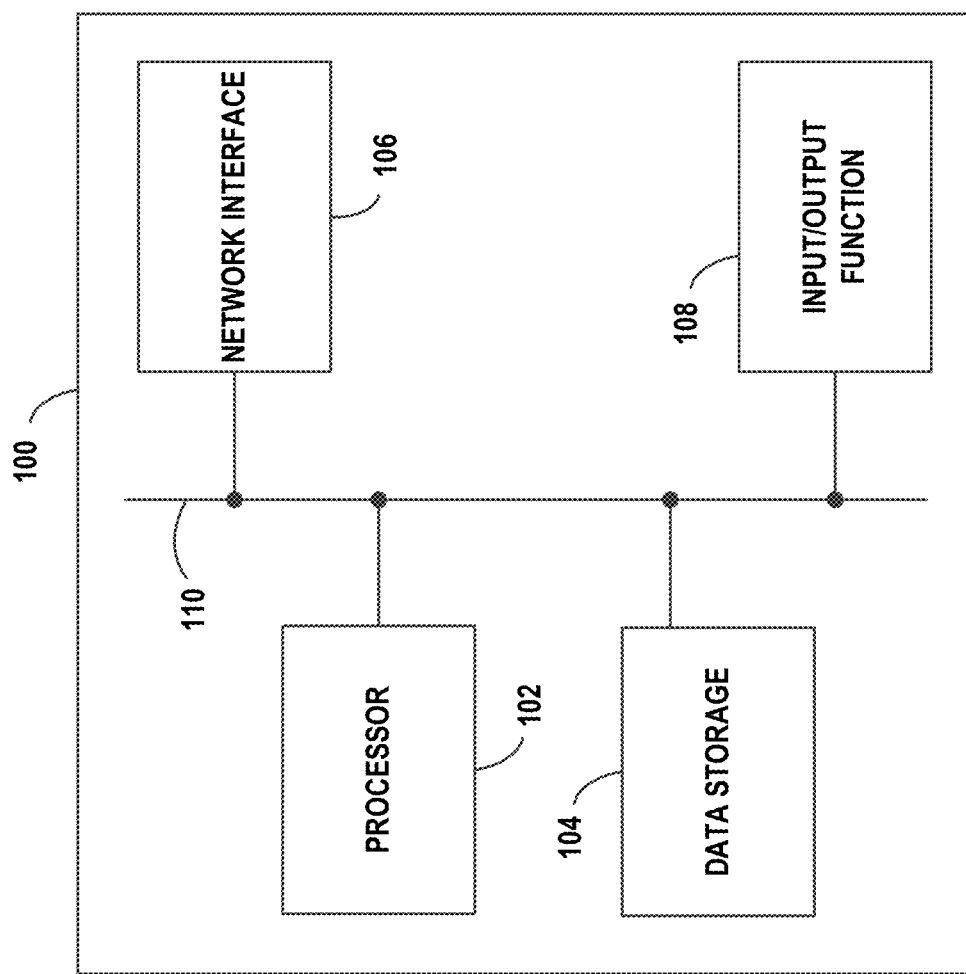
FIG. 1 illustrates a computing device, in accordance with example embodiments.

FIG. 1 is a simplified block diagram exemplifying a computing device 100, illustrating some of the functional components that could be included in a computing device arranged to operate in accordance with the embodiments herein. Example computing device 100 could be a personal computer (PC), laptop, server, or some other type of computational platform. For purposes of simplicity, this specification may equate computing device 100 to a server from time to time, and may also refer to some or all of the components of computing device 100 as a "processing unit." Nonetheless, it should be understood that the description of computing device 100 could apply to any component used for the purposes described herein.

In this example, computing device 100 includes a processor 102, a data storage 104, a network interface 106, and an input/output function 108, all of which may be coupled by a system bus 110 or a similar mechanism. Processor 102 can include one or more CPUs, such as one or more general purpose processors and/or one or more dedicated processors (e.g., application specific integrated circuits (ASICs), graphical processing units (GPUs), digital signal processors (DSPs), network processors, etc.).

Data storage 104, in turn, may comprise volatile and/or non-volatile data storage and can be integrated in whole or in part with processor 102. Data storage 104 can hold program instructions, executable by processor 102, and data that may be manipulated by these instructions to carry out the various methods, processes, or functions described herein. Alternatively, these methods, processes, or functions can be defined by hardware, firmware, and/or any combination of hardware, firmware and software. By way of example, the data in data storage 104 may contain program instructions, perhaps stored on a non-transitory, computer-readable medium, executable by processor 102 to carry out any of the methods, processes, or functions disclosed in this specification or the accompanying drawings.

Network interface 106 may take the form of a wireline connection, such as an Ethernet, Token Ring, or T-carrier connection. Network interface 106 may also take the form of a wireless connection, such as IEEE 802.11 (Wifi), BLUETOOTH®, or a wide-area wireless connection. However, other forms of physical layer connections and other types of standard or proprietary communication protocols may be used over network interface 106. Furthermore, network interface 106 may comprise multiple physical interfaces.

Input/output function 108 may facilitate user interaction with example computing device 100. Input/output function 108 may comprise multiple types of input devices, such as a keyboard, a mouse, a touch screen, and so on. Similarly, input/output function 108 may comprise multiple types of output devices, such as a screen, monitor, printer, or one or more light emitting diodes (LEDs). Additionally or alternatively, example computing device 100 may support remote access from another device, via network interface 106 or via another interface (not shown), such as a universal serial bus (USB) or high-definition multimedia interface (HDMI) port.

In some embodiments, one or more computing devices may be deployed in a networked architecture. The exact physical location, connectivity, and configuration of the computing devices may be unknown and/or unimportant to client devices. Accordingly, the computing devices may be referred to as "cloud-based" devices that may be housed at various remote locations.

Figure 2:
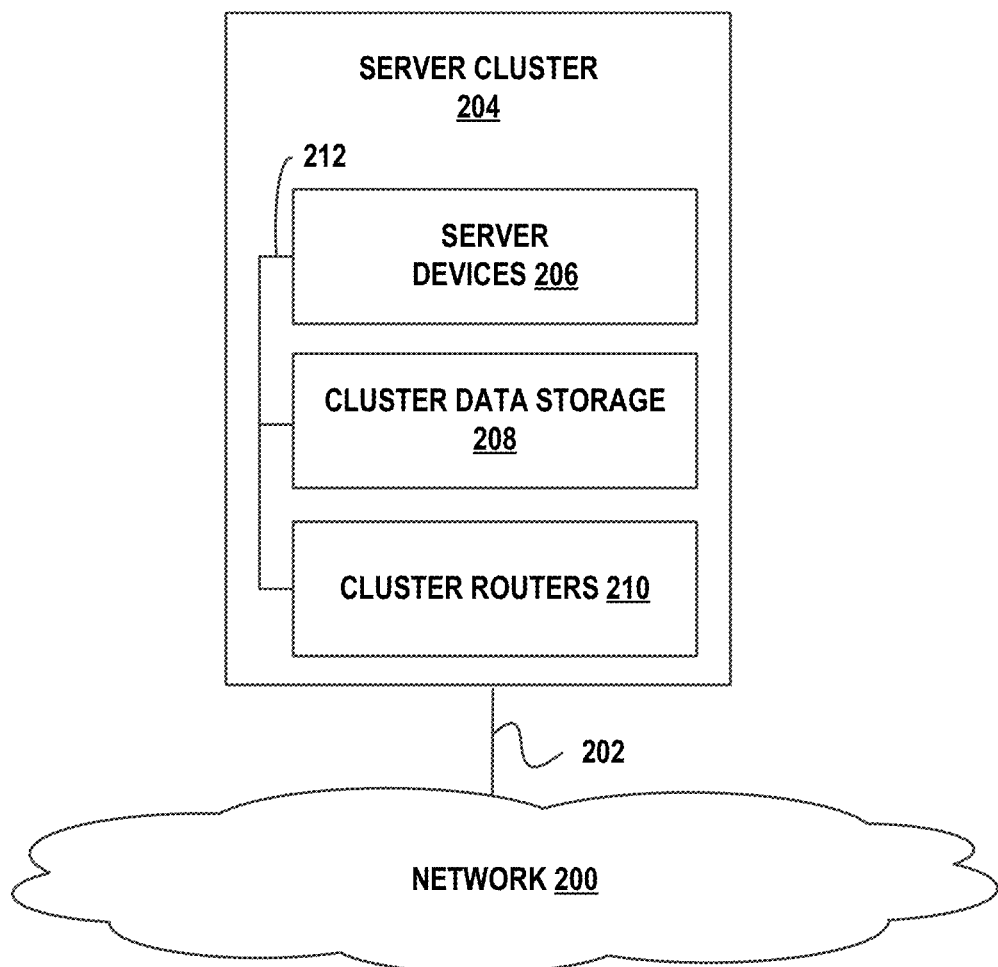
FIG. 2 illustrates a clustered computing device, in accordance with example embodiments.

FIG. 2 depicts a cloud-based server cluster 204 in accordance with an example embodiment. In FIG. 2, functions of computing device 100 may be distributed between server devices 206, cluster data storage 208, and cluster routers 210, all of which may be connected by local cluster network 212. The number of server devices, cluster data storages, and cluster routers in server cluster 204 may depend on the computing task(s) and/or applications assigned to server cluster 204.

For example, server devices 206 can be configured to perform various computing tasks of computing device 100. Thus, computing tasks can be distributed among one or more of server devices 206. To the extent that these computing tasks can be performed in parallel, such a distribution of tasks may reduce the total time to complete these tasks and return a result.

Cluster data storage 208 may be data storage arrays that include disk array controllers configured to manage read and write access to groups of hard disk drives and/or solid state drives. The disk array controllers, alone or in conjunction with server devices 206, may also be configured to manage backup or redundant copies of the data stored in cluster data storage 308 to protect against disk drive failures or other types of failures that prevent one or more of server devices 206 from accessing units of cluster data storage 208.

Cluster routers 210 may include networking equipment configured to provide internal and external communications for the server clusters. For example, cluster routers 210 may include one or more packet-switching and/or routing devices configured to provide (i) network communications between server devices 206 and cluster data storage 208 via cluster network 212, and/or (ii) network communications between the server cluster 204 and other devices via communication link 202 to network 200.

Additionally, the configuration of cluster routers 210 can be based at least in part on the data communication requirements of server devices 206 and cluster data storage 208, the latency and throughput of the local cluster network 212, the latency, throughput, and cost of communication link 202, and/or other factors that may contribute to the cost, speed, fault-tolerance, resiliency, efficiency and/or other design goals of the system architecture.

As noted, server devices 206 may be configured to transmit data to and receive data from cluster data storage 208. This transmission and retrieval may take the form of SQL queries or other types of database queries, and the output of such queries, respectively. Additional text, images, video, and/or audio may be included as well. Furthermore, server devices 306 may organize the received data into web page or web application representations. Such a representation may take the form of a markup language, such as the hypertext markup language (HTML), the extensible markup language (XML), or some other standardized or proprietary format. Moreover, server devices 206 may have the capability of executing various types of computerized scripting languages, such as but not limited to Perl, Python, PHP Hypertext Preprocessor (PUP), Active Server Pages (ASP), JAVASCRIPT®, and so on. Computer program code written in these languages may facilitate the providing of web pages to client devices, as well as client device interaction with the web pages. Alternatively or additionally, JAVA® or other languages may be used to facilitate generation of web pages and/or to provide web application functionality.

II. Example Scanning Algorithms

A body of work addresses the problem of inspection path planning for mobile robots, in which a robot scans a target object with a sensor and achieve complete coverage. The choice of sensor viewpoints and traversal paths in inspection planning are analogous to the light source vantage points and traversal paths chosen in disinfection planning. Classical coverage path planning techniques use sweeping paths to cover a large area with a sensor's viewing area, and are most applicable to problems in which the environment is roughly 2D, large compared to the viewing area, and the sensing area is roughly constant. In more complex three-dimensional scenarios, algorithms exist that iteratively use a TSP solver and viewpoint refinement technique to optimize inspection tours for unmanned aerial vehicles. A similar approach uses gradient descent to optimize path length while retaining coverage of the visible region. To achieve better global guarantees, researchers have devised asymptotically optimal sampling-based methods.

The techniques herein adopt similar path planning strategies, but rather than a binary visible/invisible criterion, the paths deliver a accumulated dosage of radiation energy to surfaces, where the irradiance smoothly varies with the distance and shape of objects. In this sense, the dosage optimization problem resembles classic approaches for radiation treatment planning for cancer therapy. In these problems, multiple radiation beams are aimed at the target tissue from many angles, but the intensity of each beam is modulated to conform to therapeutic needs. That is, the dosing should achieve a sufficient accumulation of radiation in high-dose areas (cancer) while minimizing damage to low-dose areas (noncancerous tissues). Constraints on dosing are given by the type of tissue identified through preoperative volumetric imaging, with lower bounds given for cancerous cells, upper bounds given for non-cancerous cells, and even lower upper bounds given for sensitive tissues. The present irradiation dosing problem is somewhat analogous, except that the present objective is to minimize disinfection time. However, it is quite common for there to be no solution that satisfies all of the constraints exactly, and instead the number of satisfied constraints ought to be maximized. In the field of radiation treatment planning, prior approaches have typically adopted mixed-integer programming techniques or metaheuristic optimization techniques, which are more expressive but also more computationally expensive. In settings, a goal is to improve coverage of the environment given an upper bound on the total disinfection time.

Figure 3:
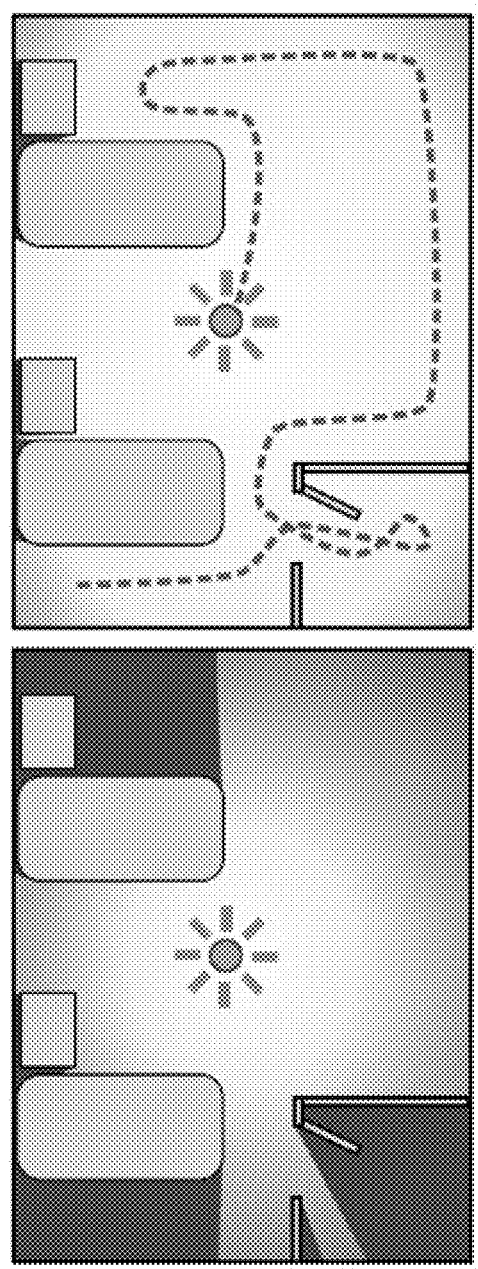
FIG. 3 illustrates how occlusions affect ultraviolet disinfection, in accordance with example embodiments.
Figure 4B:
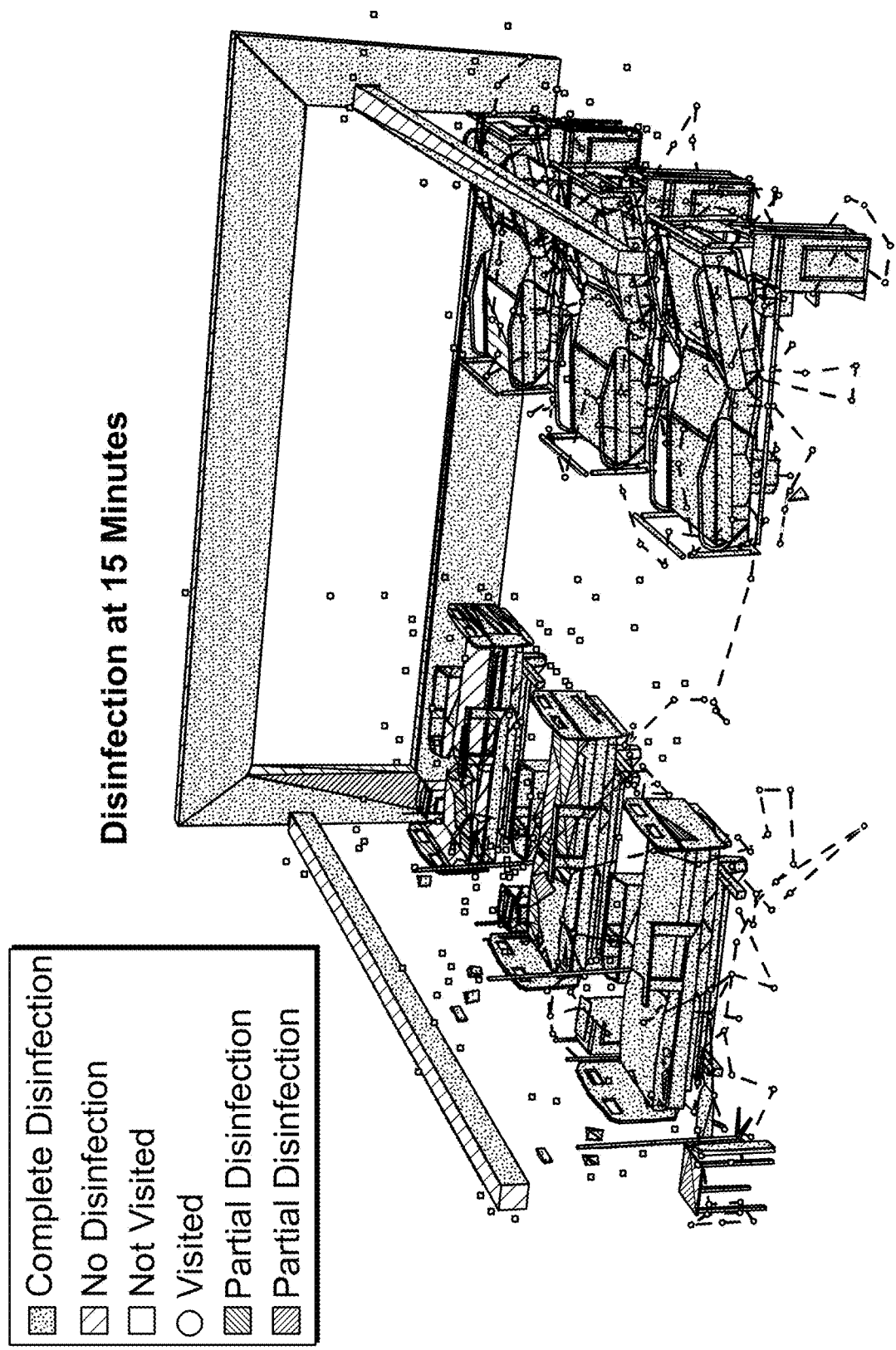
Figure 4C:
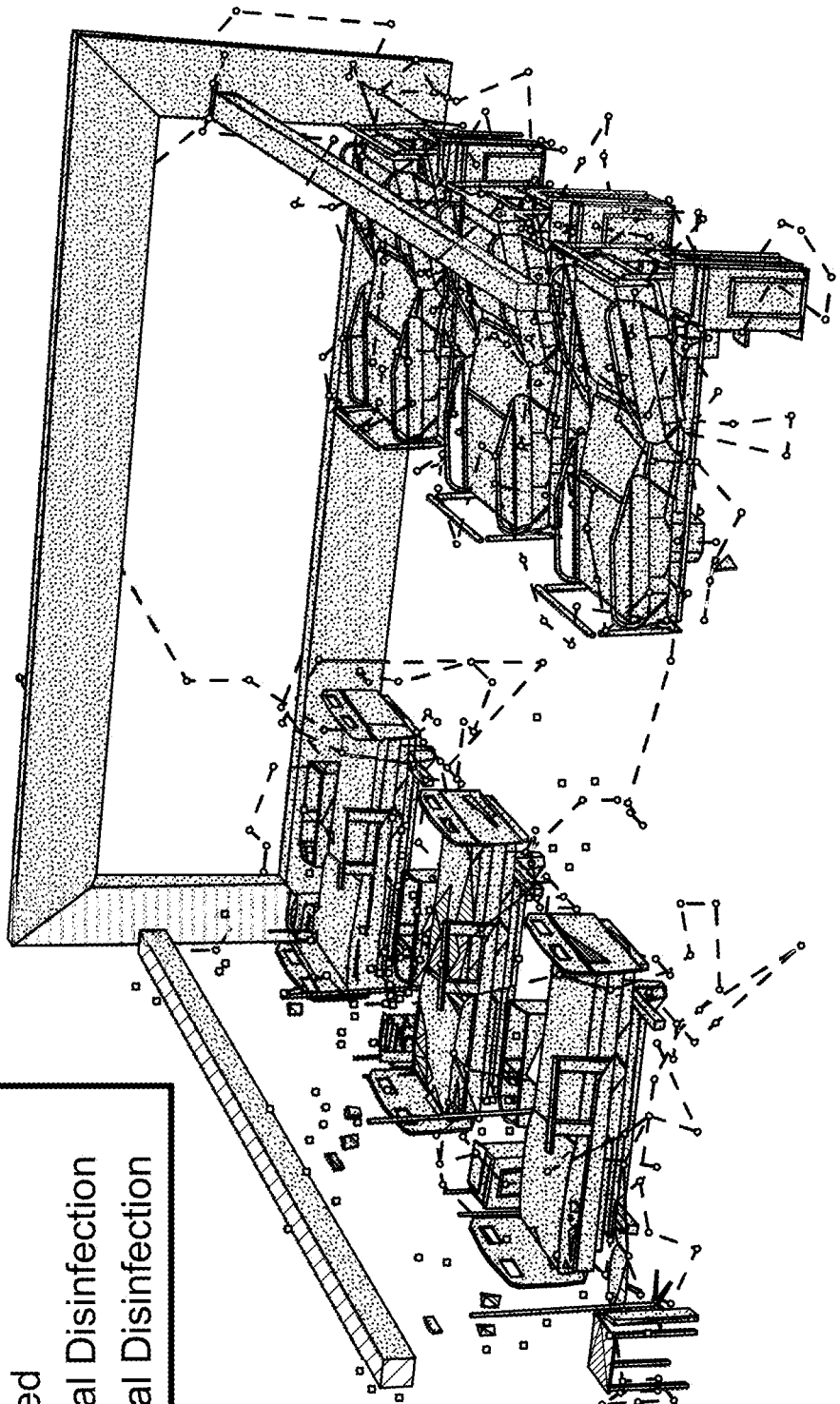
Figure 4D:
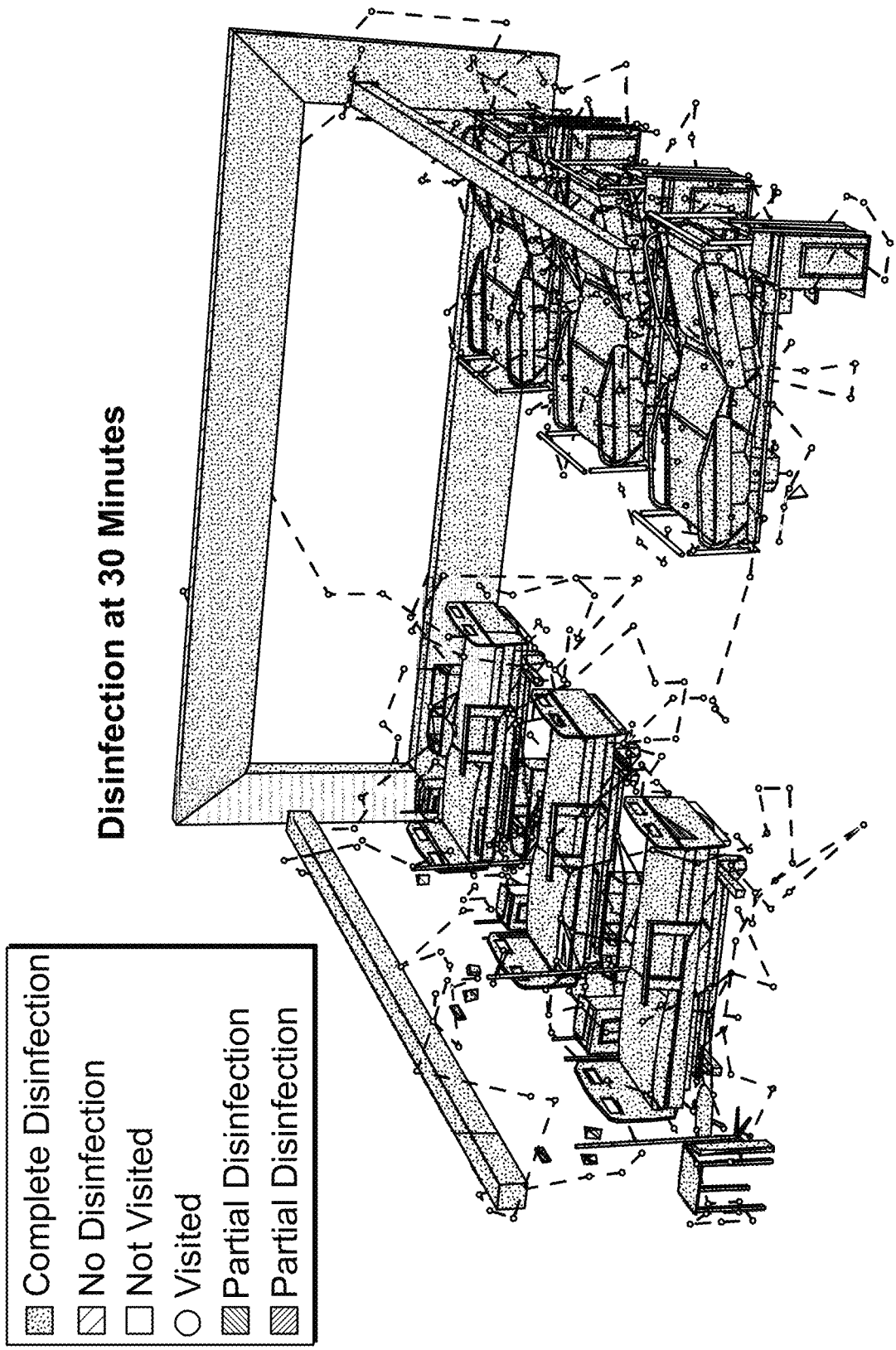

A principle behind the embodiments herein is illustrated in FIG. 3. On the left, a stationary UV light source faces occlusions and distance fall-off, so it cannot disinfect all surfaces of the environment. But on the right, a moving light source can overcome the occlusion problem and irradiate surfaces nearby, disinfecting nearly all surfaces. FIGS. 4A-4D show the efficacy of the moving light source in the form of a computer-aided design (CAD) model of a hospital room, assuming a time budget of 90 minutes. The large slanted line gradient indicates no disinfection, the dotted gradient indicates complete disinfection. The light's path is shown by the dotted line and visited dwell points are shown as circles, while unvisited ones are shown as squares.

The main algorithm has the following components. First, a three-dimensional Mapping module (3DM) acquires a three-dimensional triangular mesh model of the target environment, and annotates the mesh with an importance value indicating high-touch, low-touch, and irrelevant surfaces. Second, an Irradiance Calculation module (IC) calculates irradiance for each triangle in the three-dimensional model from a designated light source vantage point. Third, a Dosage Optimization module (DO) calculates a set of vantage points and dwell times to either minimize disinfection time to achieve a designated level of coverage, or to improve coverage given a fixed disinfection time. Fourth, a Coverage Planning module (CP) calculates an efficient path for the light positioning mechanism to traverse the vantage points selected by the dosage optimization module. Fifth, a Visualization module (VIS) displays the three-dimensional model on a screen, color-coded by quantities of interest selected by a human operator. Not all of these components need to be present in every embodiment.

Figure 5:
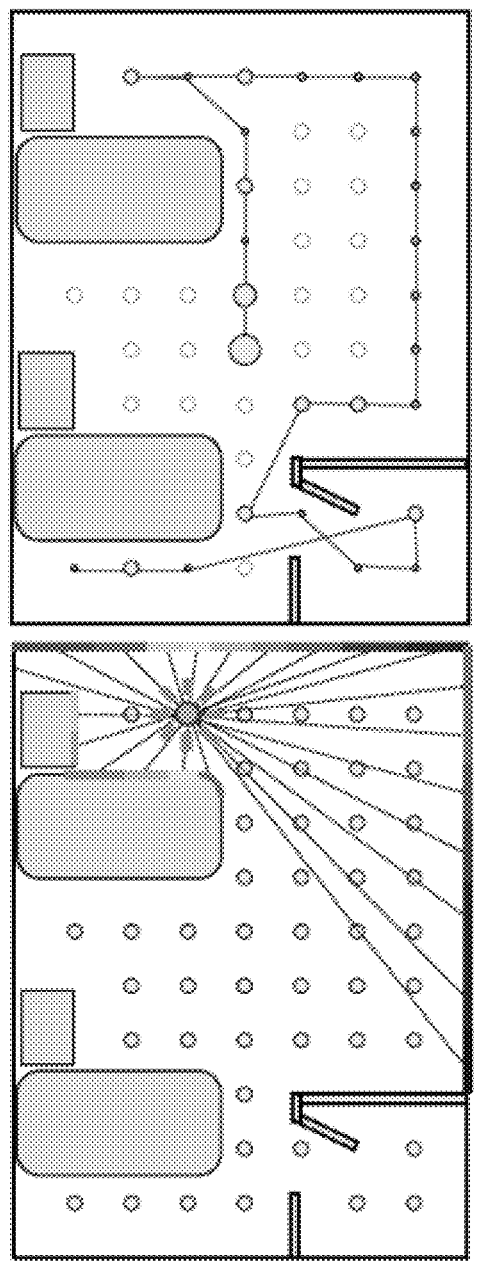
FIG. 5 illustrates dosage optimization and coverage planning, in accordance with example embodiments.

A principle behind the DO and CP embodiments are illustrated in FIG. 5. On the left, candidate vantage points are sampled. The left illustrates from the perspective of one candidate vantage point, that visibility and irradiance are calculated between each vantage point and each patch of the environment's surface. Then, on the right, an optimizer chooses dwell times for the candidate points. Non-zero dwell times are indicated by the size of each point, while zero dwell times are indicated with greyed-out circles. Then a path is generated between each point with non-zero dwell times.

As input, the method takes a description of the light source power and geometry, and a description of the light positioning mechanism in the form of 1) a kinematic and geometric model that can be used for reachability determination, and 2) a velocity limit that can be used to determine the most efficient disinfection path. The light source geometry can be modeled as an omnidirectional point, omnidirectional cylinder, or directional cylinder (e.g., fluorescent tube shielded by a parabolic mirror). If the light source is held in a person's hand, then the kinematic and geometric description may consist of an approximation of the human body with appropriate height and arm length. The method also accepts a minimum target dosage of radiant fluence for high-touch surfaces, which should be prescribed for the toughest pathogen under consideration and a desired log-reduction in microbial load.

The method can also operate in a two phase mode with separate scanning and optimization phases. First, 3DM may build a three-dimensional model of the environment in an initial scanning phase, where a sensor is moved through the environment. Second, for optimization, DO may sample a set of vantage points for the light source within the reachable free space. Third, for each vantage point, IC may be called. DO may assemble an irradiance matrix and solve an optimization problem to assign dwell times at each vantage point. Fourth, CP may find a near minimum-cost traversal path of all vantage points with non-zero dwell time. The dwell times and traversal path could then output to the light positioning mechanism. For an automated mechanism, the path may be executed directly. For a human-controlled light source, the output could be visualized on a display to guide the operator along the desired path.

The method may also operate in a live auditing mode. The live auditing mode may include 1) as the light positioning mechanism is moved through the environment, the pose of the light source in three-dimensional space, the sensor input, and the pose of the sensor are recorded; 2) upon each recorded sensor reading, the 3DM module updates the three-dimensional map; 3) IC is called on the new map and light source pose and the total radiant fluence for the three-dimensional map is updated using the latest recorded reading; 4) optionally, the radiant fluence of any newly observed triangles in the three-dimensional mesh may be initialized by calling IC with prior readings. This could be used when the light source irradiates a large portion of the environment that is not immediately viewed by the sensor; and 5) VIS displays an updated map with triangles color-coded by received radiant fluence. Similar realizations of the method, such as one-pass three-dimensional scanning and dosage optimization without a prior scanning phase, are possible.

The method could be performed in at least three different manners to provide different sets of instructions to a disinfecting agent. The embodiments could include i) how the disinfecting agent did; ii) how the disinfecting agent is currently performing; and iii) how to optimally disinfect. The operations for how the disinfecting agent did could provide feedback to a disinfecting agent on how well the agent completed disinfecting. This embodiment may include obtaining a three-dimensional map, calculating irradiance, and outputting a visualization module. The operation for how the disinfecting agent is currently performing could include providing instructions during the disinfection process for how to improve disinfection. This embodiment may include obtaining a three-dimensional map, calculating irradiance, calculating dosage optimization, and outputting a visualization module. The operation for how to optimally disinfect may instruct a disinfecting agent before and during disinfection on the best way to cover surfaces with ultraviolet light in less time. This embodiment may include obtaining a three-dimensional map, calculating irradiance, calculating dosage optimization, determining the most efficient path, and outputting a visualization module.

A. Three-Dimensional Mapping Module

The three-dimensional mapping module provides a detailed three-dimensional model of the target environment from one or more sensors moved through the environment. The mapping could be performed offline before disinfecting, or online during the disinfecting. The sensors using during mapping could include stereo cameras, laser scanners, or RGB-D cameras to provide raw color and/or depth information. The three-dimensional reconstruction of the raw data into a triangulated mesh model may be provided by photogrammetry or simultaneous localization and mapping (SLAM) techniques.

For each surface in the environment, the method may define its target dosage of radiant exposure as the product of the global target dosage and a surface-dependent importance weight that is 1 at high-touch surfaces and 0 at irrelevant surfaces. The importance weight may either be a) set by heuristics, b) derived from human annotation of the three-dimensional map, or c) by automated computer vision algorithms. Heuristics may use a database of heights and ideal heights to set importance. For example, floors and ceilings, which are outside of an ideal height range, receive importance 0 while all other surfaces may receive importance 1. Human annotation could also be obtained by a disinfection pre-survey. In the case of automated computer vision algorithms, the importance weight may be prescribed by a machine learning model, such as a neural network, trained on a training set of images and/or three-dimensional maps labeled by importance values.

B. Irradiance Calculation Model

The irradiance calculation module takes a triangulated three-dimensional mesh and a light source pose as input, and approximates the radiant flux received by each triangle in the mesh from a light source placed at that pose. The module is called thousands of times by the DO module to assemble the irradiance matrix, and in auditing mode it is called at least once for every sensor update. Therefore, it should be fast. Hence, the method may be performed on a GPU-based implementation that can perform visibility calculations in milliseconds.

The irradiance is a measure of the rate of radiant exposure, and is given in the units of watts per square meter. In an example embodiment, the irradiance may be calculated for a spherical point light at position $x \in \mathbb{R}^3$. It can be assumed that reflected light is not a major source of illumination, so that the irradiance density received by an infinitesimal patch at position $y \in \mathbb{R}^3$ with unit normal $n \in \mathbb{R}^3$ is given by:

$$I(x, y) = \begin{cases} 0 & \text{if } y \text{ is not visible from } x \\ \frac{P \cos \theta}{4\pi \|x - y\|^2} & \text{otherwise} \end{cases} \quad \text{Equation 1}$$

where P is the power (or radiant flux) of the light source and cos $$\theta = \frac{n^T(x - y)}{\|x - y\|}$$

is the cosine of the angle of incidence. A patch is considered visible only if $\cos \theta > 0$ and no other surface lies closer to x along the ray $\vec{xy}$.

$I_k(x)$ is defined as the irradiance received by a triangle k with area $A_k$ from a vantage point x. If no other triangles are in the way from x to the kth triangle, then the irradiance can be calculated. The irradiance may be calculated according to EEG and MEG: forward solutions for inverse methods. However, when occlusion occurs, no closed form solution can be found for the per-triangle irradiance. Instead, an example embodiment of the GPU-based implementation may calculate the irradiance $I_k(x)$ by rasterization. This roughly follows a common pipeline for radiosity calculations used in computer graphics but without Lambertian reflectance. The method may include the following steps:

1) The scene is rasterized using a standard graphics pipeline, with the camera centered at x. During rasterization, the three-dimensional image map may be converted into a series of pixels, dots, or lines, which, when displayed together, create an image of the scene represented via shapes, such as triangles. Each triangle's index is rendered into the pixel buffer T bound to a cubemap texture (a visibility cube) using framebuffer object. In the meantime, a Z-buffer is used for visible surface determination so that the ultimate entry T[i,j] is the closest triangle along the ray from x through pixel (i,j) on the image plane. A black pixel indicates that no triangle is occupying the pixel.

2) For each pixel T[i,j] containing a visible triangle, the amount of power e(i,j) emitted over the solid angle subtended by the pixel is precalculated and accumulated into a Shader Storage Buffer Object (SSBO) denoted as the triangle buffer F. In particular, the operation F[T[i,j]]+=e(i,j) is performed in a compute shader using a parallel prefix-sum algorithm. The accumulated value for each triangle is the radiant flux, which measures irradiance integrated over the non-occluded area of the triangle.

3) Finally, the radiant flux F[k] is divided by the area of each triangle to obtain the mean irradiance.

$$\frac{I_k}{A_k}.$$

Because this process will be performed repeatedly, the power emission e(i,j) for each pixel is precomputed into an image E of the same dimensions of the rendered buffers, so that it can be retrieved with a single memory lookup.

This method can be naturally extended to light source shapes, such as an omnidirectional cylindrical light source. In those instance, the surface of light sources can be approximated by a set of evenly distributed point sources, where each point source emits an equal fraction of the light's total radiant power. The total radiant flux is accumulated for each point before dividing by the area of each triangle to obtain the irradiance. More advanced shader programs can be used to approximate the continuous integration of light contributions along the light source's surface area on GPU.

The method can also be extended to a directional light source, such as shielded or mirrored lights. In a canonical local reference frame for the light, the luminance in each direction can be incorporated into a separate emission image for each of the six faces of the visibility cube. The emission images, $E_{+x}$, $E_{-x}$, $E_{+y}$, $E_{-y}$, $E_{+z}$, $E_{-z}$, are precomputed for the canonical reference frame, so that when the light source is oriented with rotation matrix R the visibility cube may be oriented with the same orientation, so that the modulation of the emission image respects the orientation of the light source.

C. Dosage Optimization Module

The Dosage Optimization Module (DOM) considers that the light source can be placed at a discrete set of vantage points, and adjusts the time spent at each of those points, henceforth named "dwell time." At this stage, the DOM may ignore the traversal time between vantage points. The traversal time may be the responsibility of the CP module. This formulation of the DOM assumes that the light source stops at each selected vantage point for its assigned dwell time and emits no radiation during the transition between vantage points. This is an approximation of a continuous-time problem, but if candidate vantage points are dense enough in space, then the quality of the solution approaches the true continuous-time solution. If the method assume that all vantage points are reachable, and travel time is negligible, then the DOM produces dose plans for the environment that are optimal within the sampled set of vantage points.

The DOM has two parts. A vantage point proposal step takes a three-dimensional model of the environment as input and outputs a set of candidate vantage points that will be used by the DOM. Next, the numerical optimization step takes the vantage points and three-dimensional model as input, formulates an irradiance matrix using the IC module, and then solves the optimization problem using a linear program (LP).

Vantage point proposal: The vantage point proposal step calculates a set of candidate vantage points $x_1, \ldots, x_n$, from which a subset are likely to contain an optimal dosage plan.

It is computationally advantageous to produce as few candidate vantage points as possible because it determines the number of variables used in optimization, and the size of the irradiance matrix (which is the number of triangles by the number of vintage points), which may become prohibitively large to store in a computer's memory. The method may provide a few options that may be configured as desired to produce vantage points.

1) Grid: This first option is to generate a grid of resolution h across a given bounding box. The bounding box is defined by the dimensions of the three-dimensional model and the minimum and maximum reachability of the light positioning mechanism.

2) Offset: The second option generates points that are aligned to each triangle of the three-dimensional model. For each triangle, the method may calculate a position y offset by a distance d in the triangle's normal direction away from the triangle's centroid. Amongst these points, the method may discard points that are closer than a distance r to any previously retained point.

3) Recorded path: If a prior path of the light positioning mechanism has been recorded, e.g., a manual sweep of the device through the same environment, then vantage points can be placed along the path such that they are separated by distance h. This will restrict optimization to use the same path, but reachability determination can be skipped since each pose is known to be reachable For orientable light sources (cylinders, directional cylinders) the orientation of each pose is determined as follows: with the Grid method, orientations are chosen in a fixed resolution and populated per grid point; with the Offset method, the main axis of the cylinder is aligned to the triangle, and yaw orientations of the cylinder are picked at a fixed resolution.

To check reachability of each vantage point x, the method finds a configuration of the light positioning mechanism so that it reaches the point x while not colliding with the three-dimensional model. This is done by solving an inverse kinematics (IK) problem and then performing a collision checking operation. Specifically, let $q \in C$ be a configuration of the mechanism, which has configuration space C. Furthermore, let $F \subseteq C$ be the subset of collision-free configurations. If $l(q)$ is the pose of the light source determined by forward kinematics, then IK attempts to find a $q \in F$ such that $l(q)=x$. To satisfy $l(q)=x$ the method may apply local root-finding techniques that numerically step the configuration toward a solution, starting from an initial guess go. First, the method may attempt to solve the IK problem using the last vantage configuration as an initial estimate. If IK cannot be solved or the solution includes a collision with objects in the environment, then a random $q_0$ is generated and the process is repeated until a solution is found. After some designated number of restarts, the candidate vantage point x is considered unreachable and discarded. Note that this process produces a set of feasible configurations $q_1, \ldots, q_n$ corresponding to the retained vantage points.

Numerical optimization problem: The numerical optimization step consists of a linear program that is formulated in a way that allows the system to pursue two goals: 1) disinfect the room completely, i.e., ensure that all surfaces receive the minimum disinfection fluence $\mu_{min}$, while minimizing disinfection time; 2) approximately maximize surface disinfection coverage, i.e., the fraction of all surfaces that has received min, given a fixed time budget $T_{max}$.

Let $x_1, \ldots, x_n$ be the vantage points (if the light source is not a point, $x_i$ also includes orientation), and let $t_i$ denote the dwell time at $x_i$, i.e., the amount of time that the light source spends at $x_i$ irradiating the environment. For each triangle $j=1, \ldots, m$, let $\mu_j$ be the minimum target fluence for surface disinfection.

Note that it is not always possible for every triangle to receive sufficient fluence, as some triangles are not visible from any vantage point. In an attempt to improve feasibility of the LP problem in these cases, the method may allow for partial disinfection of surfaces by introducing, for each triangle j, the slack variable $\sigma_j$, which represents the gap between the desired fluence and the actual fluence received by triangle j of a particular disinfection plan. The slack variable helps ensure that disinfection plans do not become infeasible by creating a buffer. For example, the slack variable may allow for 30% of the room to only be disinfected 80% of the way, so that disinfection can still be completed in the allotted time.

In this instance, the calculated fluence over a specific surface j is given by $\mu_j \leq \sum_{i=1}^{N}(I_{ij}t_i)+\sigma_j$. Here, I is the m×n irradiance matrix, whose columns are the irradiance vectors $I(x_i)$ calculated by IC. The resulting problem can thus be expressed as an LP over $t=(t_1, \ldots, t_n)$ and $\sigma=(\sigma_1, \ldots, \sigma_m)$.

$$\operatorname{argmin}_{t,\sigma} \sum_{i=1}^{n} t_i + D \sum_{j=1}^{m} p_j \sigma_j \qquad \text{Equation 2}$$

s.t.

$$\sum_{i=1}^{n} t_i I_{ij} + \sigma_j \geq \mu_{min} \;\; \forall \; j = 1, \ldots, m$$

$$\sum_{i=1}^{n} t_i \leq T_{max}$$

$$t, \sigma \geq 0$$

where $p_j$ denotes the priority score of a triangle j, D is a large constant, and $T_{max}$ is the time budget for disinfection. To solve the above equation, the method may leverage a large-scale LP solver algorithm.

If D is set at a high value (or equivalently, if the σ variable is removed from consideration), then the LP minimizes the time to disinfect the entire room given the time budget. If the room cannot be disinfected under the time budget, then the solution respects the time budget but minimizes the sum of products of slack variables and their priority weights. A triangle's priority score $p_j$ should, at a minimum, be proportional to its area, but can also include information like whether the triangle is a high touch or low touch surface. The value $p_j=0$ indicates that a triangle does not need disinfecting.

This formulation may not precisely take full advantage of the fraction of fully disinfected surfaces, because it views two surface patches with 50% dosages as equivalent to one patch with 100% dosage. To improve the disinfection fraction would require solving a computationally expensive Mixed Integer Linear Program (MILP). Nevertheless, the LP formulation is still is quite useful. Because empirical testing suggests that radiant dosage is roughly proportional to log-reduction in microbial load, fractional dosing leads to a disproportionate reduction in infection risk. For example, if the prescribed dose leads to a $4 \times \log_{10}$ reduction (i.e., a 99.99% reduction) in microbial load, then half the prescribed dose is still a $2 \times \log_{10}$ reduction (i.e., a 99% reduction).

One major computational challenge is that the irradiance matrix may be huge with large m and n, which can lead to large RAM usage and solve times. Sparse matrix methods reduce the cost of storing I since many triangles will have zero or very small irradiance values. However, the method may find unacceptable solve times on standard PCs when m·n is in the range of 100's of millions. To reduce m, the environment's triangle mesh may be decimated using standard mesh simplification techniques. Another option is triangle clustering so that nearby, near-coplanar triangles are grouped into a surface patch. The rows of the irradiance matrix corresponding to triangles in this patch are likely to be similar, so the method can aggregate these rows by averaging or minimizing the irradiance values.

D. Coverage Planning Module

The CP module finds a low-cost traversal of all the vantage points with nonzero dwell times using a Travelling Salesman Problem (TSP) formulation. A TSP solver takes a n×n cost matrix C where each entry $C_{ij}$ contains the distance between a precomputed path from $x_i$ to $x_j$. The TSP solver then outputs a 0-1 mask of $C_{ij}$ with paths marked by 1 forming a loop with lowest total cost among all other loops. Solving TSP exactly is NP-hard, but several practical algorithms exist with bounded suboptimality, which could be used.

Two methods could be considered to compute the paths and populate the C matrix. The first method assumes that the light positioning mechanism can move between $x_i$, $x_j$ along straight lines. The second method uses a sampling-based motion planner to precompute a network of paths among $x_1$, . . . , $_n$ and populate C with lengths of these precomputed paths. The second method is more computationally expensive, so in practice, method 1 may be attempted first before falling back to method 2 if the planner for method 1 fails.

1) Method 1: First, all of the vantage points with non-zero dwell times in each solution of Equation 2 may be defined as a set in $X_{LP}$ {$x_i|t_i \geq 0$, i=1, . . . , n}. The process in method 1 may find a tour of the light positioning mechanism through each of these configurations, starting and ending at the light positioning mechanism's current configuration. For each pair of points ($x_i$, $x_j$), a cost matrix entry $C_{ij}=\|x_i,x_j\|$ may be assigned if the straight line path between $x_i$ and $x_j$ is feasible, or ∞ otherwise. The feasibility check tests whether the segment $\overline{x_i x_j}$ can be followed directly by a feasible path in the mechanism's configuration space, beginning from configuration $q_i$ and ending at $q_j$. Given the cost matrix, an example embodiment may solve the TSP for visiting all points $x_i \in X_{LP}$. If the total length of the TSP tour of $X_{LP}$ is Λ, and the light source is always able to move at its maximum speed $v_{max}$, the total disinfection time of this method is $$T_{total} = \frac{\Lambda}{v_{max}} + \sum_{i=1}^{n} t_i \qquad \text{Equation 3}$$

2) Method 2: In method 2, an accurate network of feasible paths is built through the mechanism's configuration space to yield a better TSP cost matrix. This approach resembles the multi-goal path planning problem. Specifically, an example embodiment may generate a probabilistic roadmap R, which is a network of collision-free paths connecting feasible configurations. R is first seeded by the feasible configurations $q_1$, . . . , $q_n$ that were determined by the vantage point proposal module, restricted to the subset of vantage points with nonzero dwell time. Then, a number of new configuration samples (milestones) are progressively added to R by sampling configurations at random and retaining those configurations that are collision free. Edges between nearby configurations q and q' are then connected if the straight-line configuration-space path is completely collision free. Finally, the shortest paths within R between each pair of milestones ($q_i$, $q_j$) with i,j=1, . . . , n are determined via an all-pairs shortest path algorithm. The shortest paths may be determined for the overall shortest paths. Alternatively, the shortest paths may be determined as the shortest path from a defined starting point. The paths are further refined via a shortcutting technique. The cost matrix is populated with the lengths of these paths.

E. Visualization Module

The visualization module is a rendering of the three-dimensional model colorized by a per-triangle heat map. Following options may exist for the meaning of the heat map:

Irradiance for a given vantage point.

Total radiant exposure for a set of dwell times and vantage points, either as optimized or for a recorded path of the light source.

Ratio of target exposure (total exposure/target exposure).

Residual of exposure ratio (100%−total exposure/target exposure).

III. Experimental Results

A. Comparison Against Status Quo 1. 2.5D Experiments

In order to validate the initial hypothesis of increased disinfection efficiency, a series of initial experiments was first performed in a simplified 2.5 dimension environment. In this simplified 2.5D setting, each room consists of a 2D map representing walls of a fixed height of 2.5 meters and the UV lamp was only placed in the points belonging to the mid-plane parallel to the ground. In all of the experiments listed below, it is assume a robot that can move at a speed of 0.5 m/s, a radiant flux of 80 W for the spherical light source and a minimum disinfection fluence of 28 mj/cm².

Figure 6:
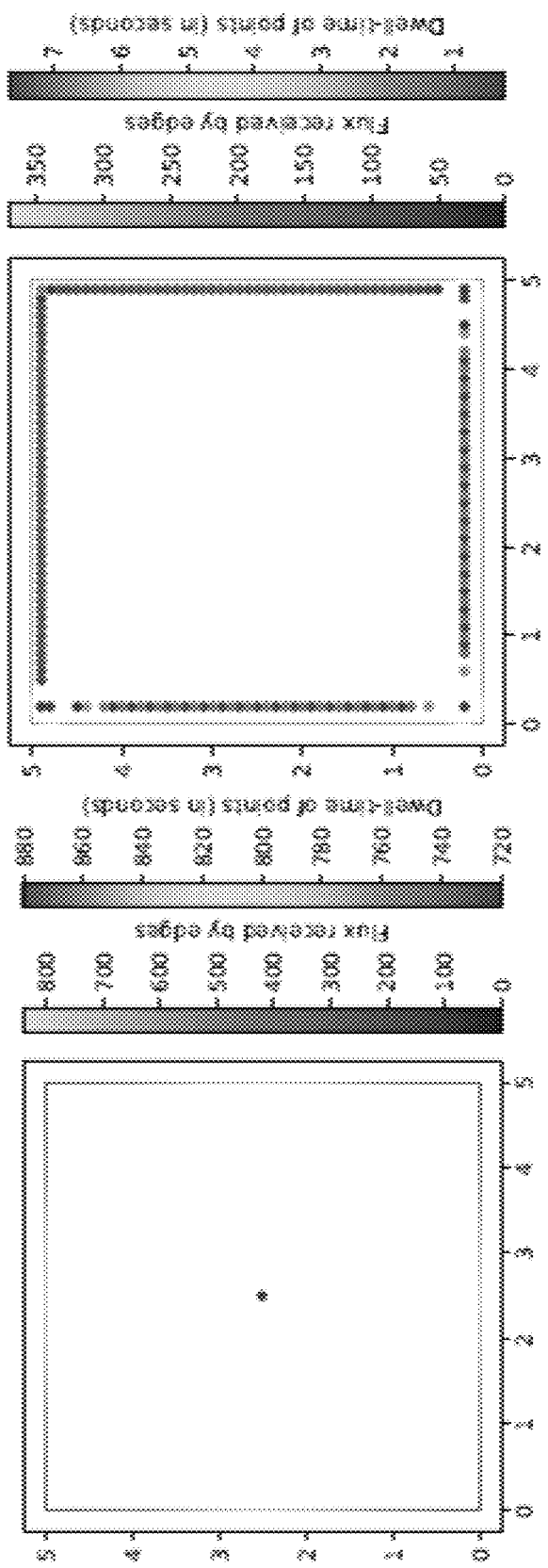
FIG. 6 illustrates disinfection of an empty square room in 2.5 dimensions, in accordance with example embodiments.

The first experiment consisted of a simple square room of dimensions 5 m×5 m with walls 2 m tall which was disinfected with two paradigms: by placing the light source in the centroid of the room and by allowing the UV lamp to follow the trajectory calculated by the method. FIG. 6 illustrates an example embodiment of a 2.5 dimension disinfection of an empty square room for single point disinfection and multipoint disinfection. In FIG. 6, vantage points are color-coded by the dwell time, and surface points are color-coded by the radiant exposure. As can be seen in FIG. 6, both methods manage to achieve the full disinfection of the room (all walls get at least 1.0 times the minimum disinfection fluence in both cases), but the single-point disinfection method requires a dwell time of 784 seconds to achieve this result, while the multipoint disinfection method can do so in only 266 seconds (including estimated movement times), around 65% faster. The single-point method underexposes the corners, so it takes 194% more time than the multipoint method. It is also notable that the multipoint method achieves a more uniform disinfection of the walls.

Figure 7:
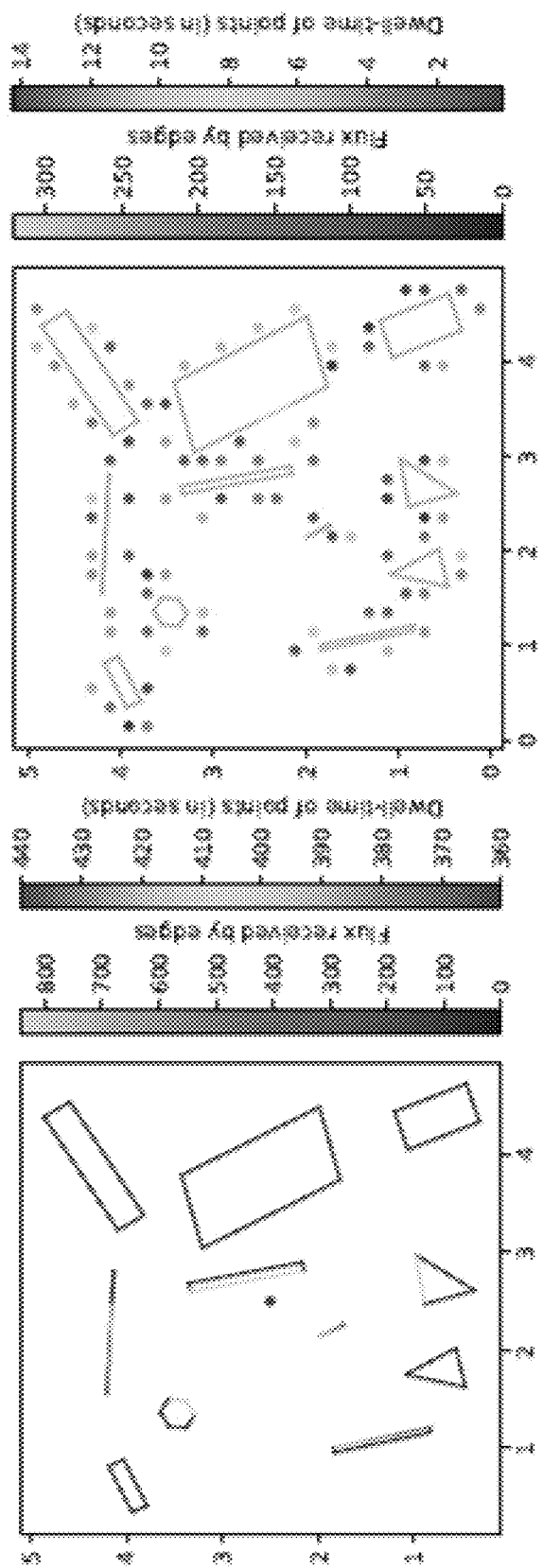
FIG. 7 illustrates disinfection of a room with randomly-generated obstacles in 2.5 dimensions, in accordance with example embodiments.

For the second set of experiments, a random room generator created 2D maps of rooms by placing randomly scaled, rotated and sheared polygonal primitives in non-colliding configurations within a room, each representing a set of 2 meter tall walls. This created more complex scenarios to evaluate the impact of occlusions on the disinfection capacity of the status-quo. An example of a 2.5 dimension disinfection of a room with randomly generated obstacles is illustrated in FIG. 7. In FIG. 7, a single point disinfection approach and a multipoint disinfection approach were given the same time budget of 400s to irradiate the room. As shown in FIG. 7, when given the same irradiation time budget required by the trajectory computed by the method to disinfect the entire room, the stationary point is only able to disinfect a small portion (20%) of it due to occlusions. Therefore, at least in this simplified version, the single-point disinfection paradigm is unable to disinfect the room, regardless of the time budget. Further experiments with other randomly generated rooms yielded similar results. After confirming these results, the pipeline was transformed to be able to work with three-dimensional environments and performed experiments in three-dimensions using CAD models of rooms.

2. Three-Dimensional Experiments

Figure 8:
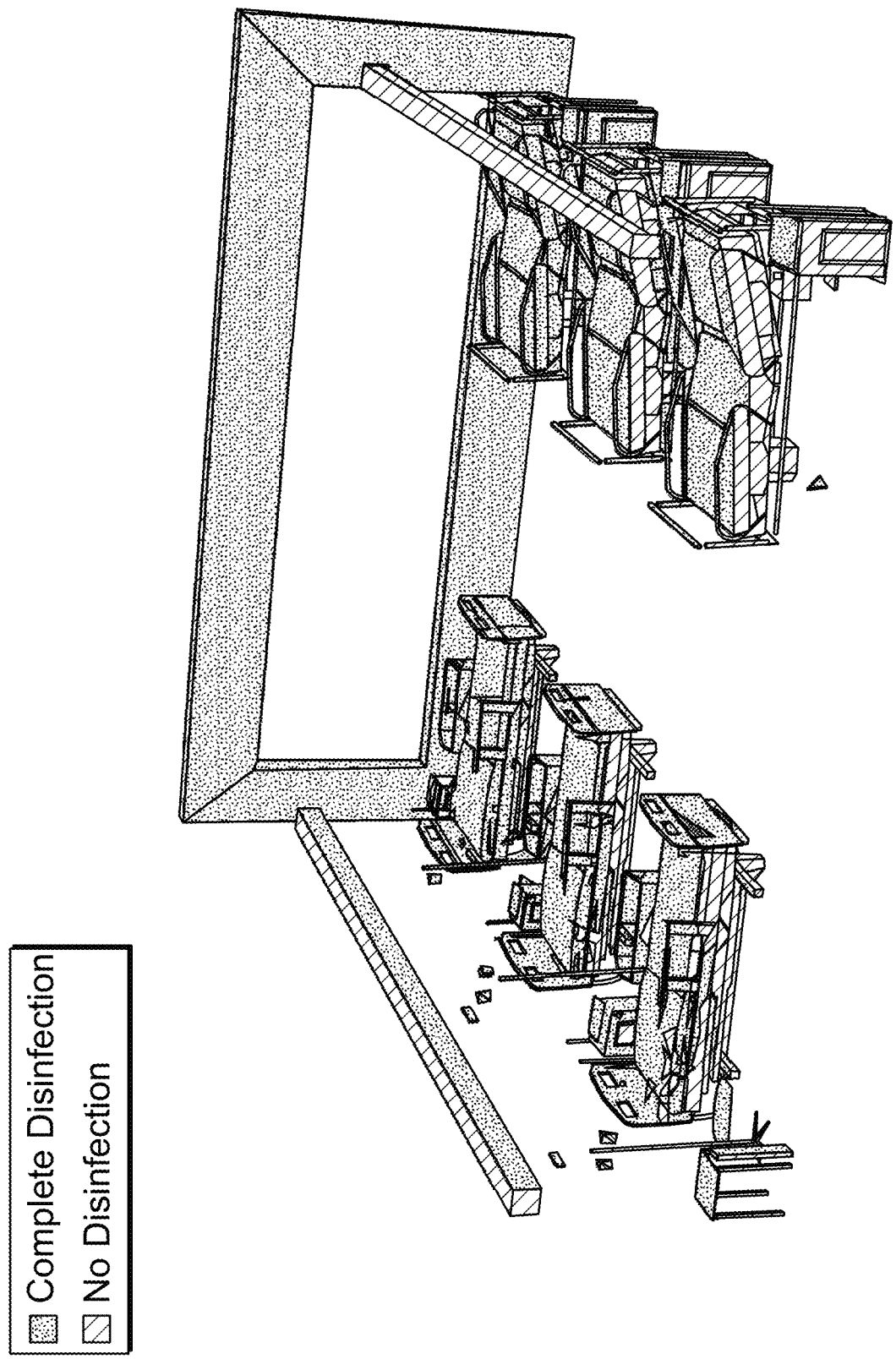
FIG. 8 illustrates disinfection with a stationary light source, in accordance with example embodiments.

As previously discussed, FIG. 4 illustrates a time-lapse of the results obtained by the present method when applied to a CAD model of a 9 m×7 m hospital room consisting of six beds, bedside tables, and IV stands. This is a particularly challenging scenario with many occlusions. Most walls and floors are excluded from the disinfection. The present method finds a path and dwell times for the light source within minutes and is able to disinfect more than 70% of the environment's surface area within 30 minutes. In this experiment, the method considered a light source whose radiant flux P is equal to 80 W and a target disinfection fluence of 28 mj/cm$^2$, which targets approximately a 3×log$_{10}$ in infectivity of SARS-COV2. In contrast, FIG. 8 illustrates the same scenario but with a stationary light source at the center of the room and at mid-height. Given the same time budget of 30 minutes, the light disinfects only 35% of the environment, leaving far corners, obliquely-oriented surfaces, and occluded surfaces underexposed (seen in the figure as a large slanted line gradient, as opposed to properly irradiated surfaces, represented as a small dot gradient). These results indicate that the benefits observed for the method over the status-quo in 2.5D seem to also be present in full three-dimensional environments.

B. Golden Standard Solution Description: MILP

Rather than separately defining a separate dwell time optimization and coverage planning optimization, the UV disinfection problem can be formulated as a unified optimization problem where the time to traverse the vantage points is also included in the objective function. For any objective (minimizing overall time or maximizing coverage with a time budget), the optimal unified solution may improve the result computed by the two-stage technique, but computing the true optimal solution is computationally expensive except for very small problems. The following section describes the mathematical formulation of the unified optimization approach and experiments comparing it to the two-stage approach.

Again the vantage points are defined as $x_1, \ldots, x_n$, and the cost matrix C is defined to assign time durations to each local path connecting vantage points. An example embodiment attempts to find both dwell times at each point t and a trajectory L through every point with a nonzero dwell time. The trajectory L is given by a sequence of vantage point indices $L=(L_1, \ldots, L_{|L|})$. Then, the total disinfection time is equal to the sum of the dwell times plus the travel time between points in L. Using this, an optimization problem can be formulated, which encodes both the LP and the TSP, to minimize total disinfection time:

$$\text{argmin}_{L,t} \sum_{i=1}^{n} t_i + \sum_{k=1}^{|L|=1} C_{L_k L_{k+1}} \quad \text{Equation 4}$$

-continued $$\text{s.t. } \mu_j \leq \sum_{i=1}^{n} l_{ij} t_i \ \forall \ j = 1, \ldots, m$$

$$t \geq 0$$

$$L_k \in \{1, \ldots, n\} \ \forall \ j = 1, \ldots, |L|$$

$$t_j = 0 \text{ if } j \notin L \ \forall \ j = 1, \ldots, m$$

The initial and terminal configurations of the trajectory can also be constrained to lie at the device's given configuration by defining a "virtual vantage point" $x_1$ but excluding the dosage constraint for j=1, and requiring that $L_1 = L_{|L|} = 1$.

When formulating the above equations, the challenge is that the sequence is variable length, and that the device can only emit power at points in the sequence L. TSP problems have been solved using a variety of mixed integer linear programming (MILP) formulations. However, these formulations cannot be used directly for the method because the method needs to find a path passing only a subset of vertices, not all vertices.

It is common in TSP-like problems to introduce variables to mark edge selection. In an example embodiment, the method may introduce 2|E| binary decision variables:

$$e_{ij} \in \{0,1\} \forall i \neq j \quad \text{Equation 5}$$

where $e_{ij}$ indicates whether an edge is in the path. That is, $e_{ij}=1$ if and only if $L_k=i$ and $L_{k+1}=j$ for some $k \in \{1, \ldots, |L|-1\}$. Note that the method uses two variables $e_{ij}$, $e_{ji}$ for each physical path between vertices, and which one is selected determines the directionality of the path. It can be inferred whether $x_i$ is selected from $e_{ij}$ by noting that $x_i \in L$ if and only if $\Sigma_{j=1}^{n} e_{ij}=1$.

With this, the final constraint (that power can only be emitted at vertices in L) is converted to the following constraints:

$$0 \leq t_i \leq M \sum_{j=1}^{n} e_{ij} \ \forall \ i = 1, \ldots, n, \quad \text{Equation 6}$$

where M is a big constant (e.g. set M=1000 indicating that the path will not dwell at a vertex for more than 1000 s). The method may further require that the light should move in a closed loop starting and ending at $x_1$ by imposing the constraint:

$$\sum_{j=1}^{n} e_{ij} = 1 \quad \text{Equation 7}$$

To impose the constraint that the path forms a simple loop, the method should first ensure that each selected vertex has degree two, which converts to:

$$\sum_{j=1}^{n} e_{ij} = \sum_{j=1}^{n} e_{ji} \ \forall \ i = 1, \ldots, N \quad \text{Equation 8}$$

$$\sum_{j=1}^{n} e_{ij} \leq 1 \ \forall \ i = 1, \ldots, N,$$

The idea here is that each vertex $x_1$ is connected to the same amount of incoming edges and outgoing edges (first line), and the number of incoming edges is at most 1 (second line). If and only if the number of incoming edges is 1, then vertex i is selected as part of the path.

A challenge in TSP is to ensure that there are no independent loops (e.g. $e_{23}=e_{34}=e_{42}=1$). To this end, the method may utilize a single-commodity flow (SCF) formulation. The idea behind the SCF is to require the disinfecting agent to carry some amount of goods and it needs to unload a unit amount of goods to each selected vertex $i \in L$ (similar to the network-flow constraint). To model this behavior, continuous variables $g_{ij}$ may be introduced to represent the amount of goods the disinfecting agent is carrying when traveling from vertex i to j. If the following constraint is introduced:

$$\sum_{j=1}^{n} g_{ji} - \sum_{j=1}^{n} g_{ji} = \sum_{j=1}^{n} e_{ij} \ \forall \ i = 2, \ldots, N \quad \text{Equation 9}$$

$$0 \le g_{ij} \le Me_{ij} \ \forall \ i \ne j$$

$$g_{ij} \le \frac{\sum_{i=1}^{n} \sum_{j=1, j \ne i}^{n} e_{ij}}{2} - 1 \ \forall \ i \ne j$$

then the solution should contain only one simple loop. The first line implies that if vertex i is selected, then the agent will carry one unit fewer amount of goods when leaving this vertex. The second line means that when an edge is not selected, then the agent cannot carry any goods along it. The third line implies that the agent will carry just enough amount of goods. To understand this, note that each selected vertex has one incoming edge and one outgoing edge. Therefore, the total number of vertices belonging to L is $\sum_{i=1}^{n}\sum_{j=1,j \ne i}^{n} e_{ij}/2$. In order to unload a unit amount of goods to each vertex (other then the first one), the agent needs to carry exactly $\sum_{i=1}^{n}\Sigma_{j=1,j \ne i}^{n} e_{ij}/2-1$ amount of goods.

Altogether, the MILP formulation solves the following problem:

$$\operatorname{argmin}_{L,t} \sum_{i=1}^{n} t_i + \sum_{k=1}^{|L|=1} C_{L_k L_{k+1}} \quad \text{Equation 10}$$

$$\text{s.t.} \ \mu_j \le \sum_{i=1}^{n} I_{ij} t_i \ \forall \ j = 1, \ldots, m$$

$$t \ge 0$$

Equations 6, 7, 8, and 9 hold where e collects all $e_{ij}$ Boolean variables and g collects all $g_{ij}$ variables. The method may be solved using a fast commercial solver that handles MILPs.

C. Comparisons to the Optimal Solution

As stated in the previous section, sequentially optimizing dwell times and tour paths yields suboptimal results when compared to the golden standard described above. Even though the method already outperformed the status-quo in terms of disinfection time and coverage, the method could potentially be improved. A plurality of 2.5D rooms were randomly generated to produce a set of example rooms to which both the sequential method and the joint optimization via MILP were applied. It is worth noting that it would be computationally intractable to perform these studies with three-dimensional rooms.

Figure 9:
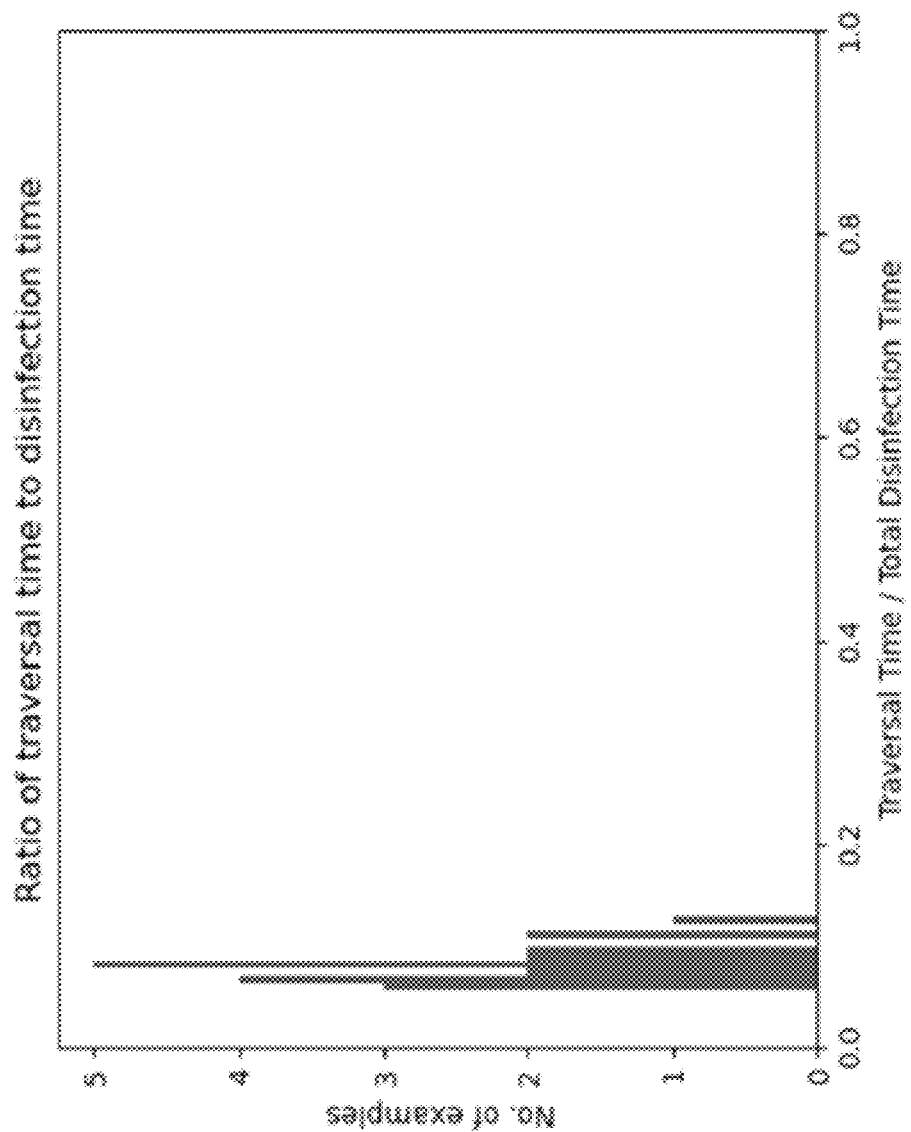
FIG. 9 illustrates a histogram of the fraction of time taken by movement during the disinfection of a set of 21 randomly generated 2.5 dimensional rooms, in accordance with example embodiments.
Figure 10:
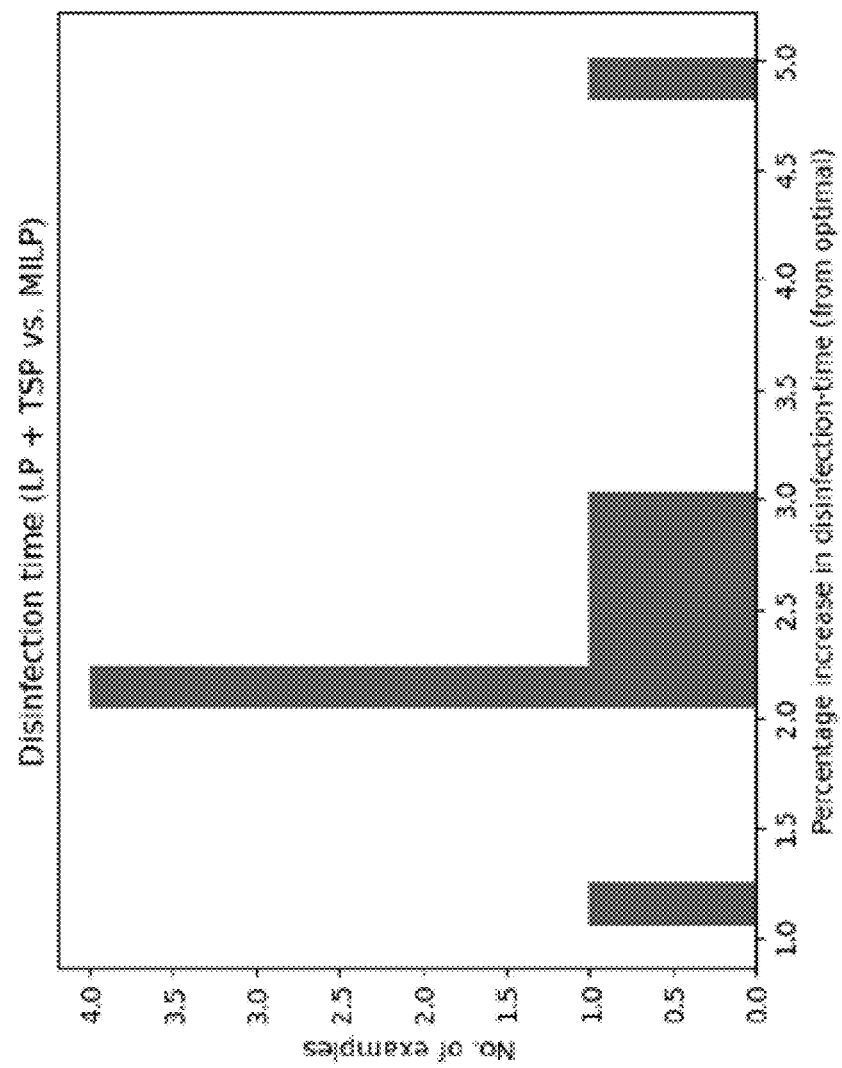
FIG. 10 illustrates a histogram of the time taken by a sequential approach compared to an optimized approach, in accordance with example embodiments.

Experiments calculated the fraction of total disinfection time that was taken by movement, excluding dwell time at the vantage points. FIG. 9 illustrates a histogram of the fraction of time taken by movement during the disinfection of a set of twenty-one randomly generated 2.5D rooms. FIG. 9, illustrates that, in most cases, the time required by movement around the room was usually below 10% of the total disinfection time. As an additional step, 10 of those rooms were randomly selected and the optimal solution was calculated for each of them using the MILP above. FIG. 10 illustrates an additional histogram of the extra time taken by the sequential approach when compared to the optimal solution. As expected, the sequential optimization took at most 5% longer to fully disinfect the rooms, which is in line with the preliminary results. However, the MILP solve times were orders of magnitude higher than the sequential optimization method, taking minutes to hours to solve. Therefore, in practice the benefit of solving plans quickly outweighs the small gains in disinfection times afforded by using the MILP formulation.

IV. Example Operations

Figure 11:
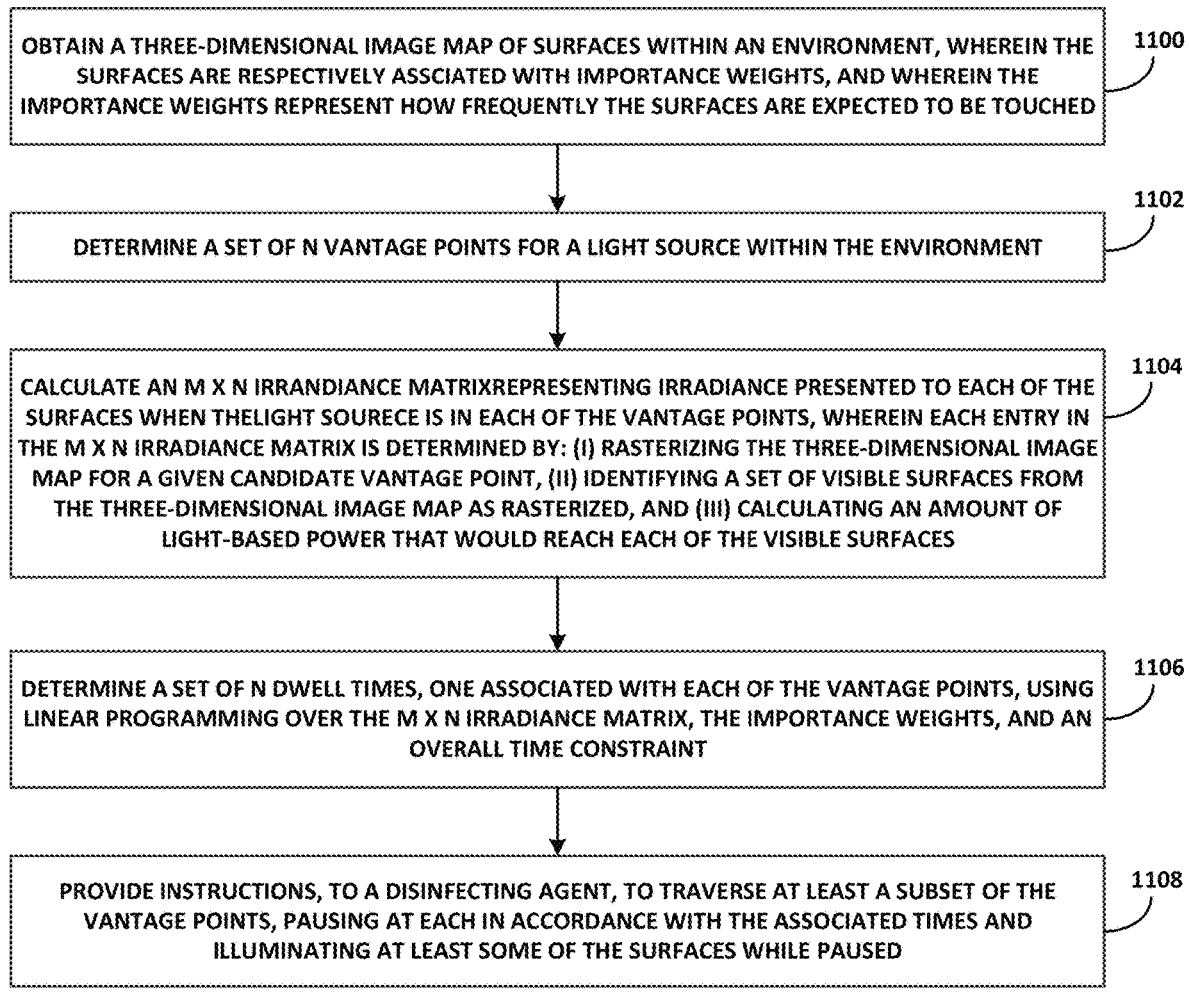
FIG. 11 is a flow chart, in accordance with example embodiments.

FIG. 11 is a flow chart illustrating an example embodiment. The process illustrated by FIG. 11 may be carried out by a computing device, such as computing device 100, and/or a cluster of computing devices, such as server cluster 200. However, the process can be carried out by other types of devices or device subsystems. For example, the process could be carried out by a portable computer, such as a laptop or a tablet device.

The embodiments of FIG. 11 may be simplified by the removal of any one or more of the features shown therein. Further, these embodiments may be combined with features, aspects, and/or implementations of any of the previous figures or otherwise described herein.

Block 1100 may involve obtaining a three-dimensional image map of m surfaces within an environment, wherein the surfaces are respectively associated with importance weights, and wherein the importance weights represent how frequently the surfaces are expected to be touched.

Block 1102 may involve determining a set of n vantage points for a light source within the environment.

Block 1104 may involve calculating an m×n irradiance matrix representing irradiance presented to each of the surfaces when the light source is in each of the vantage points, wherein each entry in the m×n irradiance matrix is determined by: (i) rasterizing the three-dimensional image map for a given candidate vantage point, (ii) identifying a set of visible surfaces from the three-dimensional image map as rasterized, and (iii) calculating an amount of light-based power that would reach each of the visible surfaces.

Block 1106 may involve determining a set of n dwell times, one associated with each of the vantage points, using linear programming over the m×n irradiance matrix, the importance weights, and an overall time constraint.

Block 1108 may involve providing instructions, to a disinfecting agent, to traverse at least a subset of the vantage points, pausing at each in accordance with the associated dwell times and illuminating at least some of the surfaces while paused.

Some embodiments may involve displaying a visualization of the three-dimensional image map, wherein the instructions are color coded on the visualization of the three-dimensional image map.

In some embodiments, displaying the visualization involves displaying portions of the three-dimensional image map with the vantage points that the disinfecting agent has not yet traversed or to which the disinfecting agent is to return.

In some embodiments, obtaining the three-dimensional image map comprises moving one or more sensors about the environment, wherein the one or more sensors detect and gather three-dimensional spatial layout information about the environment. In some embodiments, the one or more sensors include at least one of a stereo camera, a laser scanner, or an RGB-D camera.

In some embodiments, the linear programming allows for partial disinfection of the surfaces with a slack variable, and wherein the slack variable is a difference between target radiant fluences for the surfaces and proposed radiant fluences to be provided to the surfaces while the disinfecting agent is paused.

Some embodiments may involve forming a further subset of the vantage points by removing vantage points with non-zero dwell times from the subset of the vantage points, and based on a travelling salesman algorithm, determining, for the disinfecting agent, a traversal path of the further subset of the vantage points. In some embodiments, the traversal path includes a probabilistic roadmap, wherein the probabilistic roadmap is determined by (i) considering the further subset of the vantage points, (ii) adding sample configurations of the further subset of vantage points to the probabilistic roadmap that do not intersect objects in the environment, (iii) connecting the vantage points in the sample configurations that can be connected with a straight line that does not intersect objects in the environment, and (iv) determining shortest paths between the vantage points in the sample configurations. In some embodiments the sample configurations comprise different orders of traversing the further subset of the vantage points. In some embodiments, the new samples of configurations of the subset are progressively added to the probabilistic roadmap by sampling configurations at random.

In some embodiments, the disinfecting agent is a mobile robot configured to cause emission of ultraviolet light when dwelling at each of the subset of the vantage points.

In some embodiments, the disinfecting agent is a person instructed to cause emission of ultraviolet light when dwelling at each of the subset of the vantage points and equipped with at least one of an ultraviolet disinfection push-cart or an ultraviolet disinfection wand.

In some embodiments, the importance weights are set by user input comprising importance annotations on the three-dimensional image map.

In some embodiments, the importance weights are set by a machine learning model, and wherein the machine learning model comprises a neural network trained on a training set of three-dimensional image maps with surfaces thereof labeled with importance values.

In some embodiments, determining the set of n vantage points further involves: based on a power and a geometry of the light source, determining reachabilities of the light source to the surfaces from the vantage points; and considering vantage points that satisfy the reachabilities.

In some embodiments, the light source is at least one of an omnidirectional point source, an omnidirectional cylindrical source, or a directional cylindrical source.

In some embodiments, the vantage points are respectively associated with one or more orientations of the light source, and wherein determining the set of vantage points comprises: generating a grid over the three-dimensional image map based on a reachability of the light source; and for each location in the grid, determining a plurality of orientations of the light source.

In some embodiments, the surfaces are represented as triangles, wherein the vantage points are respectively associated with one or more orientations of the light source, and wherein determining the one or more orientations for a particular vantage point comprises: determining, for each triangle: (i) an offset for the light source in a nominal direction away a centroid of the triangle, (ii) an axis of alignment of the light source along a leg of the triangle, and (iii) one or more rotational positions of the light source as aligned and as positioned at the offset.

Some embodiments may involve determining the dwell times based on a predetermined target dosage of radiant fluence for high-touch surfaces.

V. Conclusion

The present disclosure is not to be limited in terms of the particular embodiments described in this application, which are intended as illustrations of various aspects. Many modifications and variations can be made without departing from its scope, as will be apparent to those skilled in the art. Functionally equivalent methods and apparatuses within the scope of the disclosure, in addition to those described herein, will be apparent to those skilled in the art from the foregoing descriptions. Such modifications and variations are intended to fall within the scope of the appended claims.

The above detailed description describes various features and operations of the disclosed systems, devices, and methods with reference to the accompanying figures. The example embodiments described herein and in the figures are not meant to be limiting. Other embodiments can be utilized, and other changes can be made, without departing from the scope of the subject matter presented herein. It will be readily understood that the aspects of the present disclosure, as generally described herein, and illustrated in the figures, can be arranged, substituted, combined, separated, and designed in a wide variety of different configurations.

With respect to any or all of the message flow diagrams, scenarios, and flow charts in the figures and as discussed herein, each step, block, and/or communication can represent a processing of information and/or a transmission of information in accordance with example embodiments. Alternative embodiments are included within the scope of these example embodiments. In these alternative embodiments, for example, operations described as steps, blocks, transmissions, communications, requests, responses, and/or messages can be executed out of order from that shown or discussed, including substantially concurrently or in reverse order, depending on the functionality involved. Further, more or fewer blocks and/or operations can be used with any of the message flow diagrams, scenarios, and flow charts discussed herein, and these message flow diagrams, scenarios, and flow charts can be combined with one another, in part or in whole.

A step or block that represents a processing of information can correspond to circuitry that can be configured to perform the specific logical functions of a herein-described method or technique. Alternatively or additionally, a step or block that represents a processing of information can correspond to a module, a segment, or a portion of program code (including related data). The program code can include one or more instructions executable by a processor for implementing specific logical operations or actions in the method or technique. The program code and/or related data can be stored on any type of computer readable medium such as a storage device including RAM, a disk drive, a solid state drive, or another storage medium.

The computer readable medium can also include non-transitory computer readable media such as computer readable media that store data for short periods of time like register memory and processor cache. The computer readable media can further include non-transitory computer readable media that store program code and/or data for longer periods of time. Thus, the computer readable media may include secondary or persistent long term storage, like ROM, optical or magnetic disks, solid state drives, or compact-disc read only memory (CD-ROM), for example. The computer readable media can also be any other volatile or non-volatile storage systems. A computer readable medium can be considered a computer readable storage medium, for example, or a tangible storage device.

Moreover, a step or block that represents one or more information transmissions can correspond to information transmissions between software and/or hardware modules in the same physical device. However, other information transmissions can be between software modules and/or hardware modules in different physical devices.

The particular arrangements shown in the figures should not be viewed as limiting. It should be understood that other embodiments can include more or less of each element shown in a given figure. Further, some of the illustrated elements can be combined or omitted. Yet further, an example embodiment can include elements that are not illustrated in the figures.

While various aspects and embodiments have been disclosed herein, other aspects and embodiments will be apparent to those skilled in the art. The various aspects and embodiments disclosed herein are for purpose of illustration and are not intended to be limiting, with the true scope being indicated by the following claims.

What is claimed is:

1. A computer-implemented method comprising:
   obtaining a three-dimensional image map of m surfaces within an environment, wherein the surfaces are respectively associated with importance weights, and wherein the importance weights represent how frequently the surfaces are expected to be touched;
   determining a set of n vantage points for a light source within the environment;
   calculating an m×n irradiance matrix representing irradiance presented to each of the surfaces when the light source is in each of the vantage points, wherein each entry in the m×n irradiance matrix is determined by: (i) rasterizing the three-dimensional image map for a given candidate vantage point, (ii) identifying a set of visible surfaces from the three-dimensional image map as rasterized, and (iii) calculating an amount of light-based power that would reach each of the visible surfaces;
   determining a set of n dwell times, one associated with each of the vantage points, using linear programming over the m×n irradiance matrix, the importance weights, and an overall time constraint; and
   providing instructions, to a disinfecting agent, to traverse at least a subset of the vantage points, pausing at each in accordance with the associated dwell times and illuminating at least some of the surfaces while paused.

2. The computer-implemented method of claim 1, further comprising:
   displaying a visualization of the three-dimensional image map, wherein the instructions are color coded on the visualization of the three-dimensional image map.

3. The computer-implemented method of claim 2, further comprising:
   displaying portions of the three-dimensional image map, wherein the surfaces that the disinfecting agent has not yet illuminated or to which the disinfecting agent is to return are color coded on the visualization of the three-dimensional image map.

4. The computer-implemented method of claim 1, wherein obtaining the three-dimensional image map comprises moving one or more sensors about the environment, wherein the one or more sensors detect and gather three-dimensional spatial layout information about the environment.

5. The computer-implemented method of claim 4, wherein the one or more sensors include at least one of a stereo camera, a laser scanner, or an RGB-D camera.

6. The computer-implemented method of claim 1, wherein the linear programming allows for partial disinfection of the surfaces with a slack variable, and wherein the slack variable is a difference between target radiant fluences for the surfaces and proposed radiant fluences to be provided to the surfaces while the disinfecting agent is paused.

7. The computer-implemented method of claim 1, further comprising:
   forming a further subset of the vantage points by removing vantage points with non-zero dwell times from the subset of the vantage points; and
   based on a travelling salesman algorithm, determining, for the disinfecting agent, a traversal path of the further subset of the vantage points.

8. The computer-implemented method of claim 7, wherein the traversal path comprises a probabilistic roadmap, wherein the probabilistic roadmap is determined by (i) considering the further subset of the vantage points, (ii) adding sample configurations of the further subset of vantage points to the probabilistic roadmap that do not intersect objects in the environment, (iii) connecting the vantage points in the sample configurations that can be connected with a straight line that does not intersect objects in the environment, and (iv) determining shortest paths between the vantage points in the sample configurations.

9. The computer-implemented method of claim 8, wherein the sample configurations comprise different orders of traversing the further subset of the vantage points.

10. The computer-implemented method of claim 8, wherein the new samples of configurations of the subset are progressively added to the probabilistic roadmap by sampling configurations at random.

11. The computer-implemented method of claim 1, wherein the disinfecting agent is a mobile robot configured to cause emission of ultraviolet light when dwelling at each of the subset of the vantage points.

12. The computer-implemented method of claim 1, wherein the disinfecting agent is a person instructed to cause emission of ultraviolet light when dwelling at each of the subset of the vantage points and equipped with at least one of an ultraviolet UV disinfection push-cart, or an ultraviolet UV disinfection wand.

13. The computer-implemented method of claim 1, wherein the importance weights are set by user input comprising importance annotations on the three-dimensional image map.

14. The computer-implemented method of claim 1, wherein the importance weights are set by a machine learning model, and wherein the machine learning model comprises a neural network trained on a training set of three-dimensional image maps with surfaces thereof labeled with importance values.

15. The computer-implemented method of claim 1, wherein determining the set of n vantage points further comprises:
   based on a power and a geometry of the light source, determining reachabilities of the light source to the surfaces from the vantage points;
   considering vantage points that satisfy the reachabilities.

16. The computer-implemented method of claim 1, wherein the light source is at least one of an omnidirectional point source, an omnidirectional cylindrical source, or a directional cylindrical source.

17. The computer-implemented method of claim 1, wherein the vantage points are respectively associated with one or more orientations of the light source, and wherein determining the set of vantage points comprises:
   generating a grid over the three-dimensional image map based on a reachability of the light source; and
   for each location in the grid, determining a plurality of orientations of the light source.

18. The computer-implemented method of claim 1, wherein the surfaces are represented as triangles, wherein the vantage points are respectively associated with one or more orientations of the light source, and wherein determining the one or more orientations for a particular vantage point comprises:
   determining, for each triangle: (i) an offset for the light source in a nominal direction away a centroid of the triangle, (ii) an axis of alignment of the light source along a leg of the triangle, and (iii) one or more rotational positions of the light source as aligned and as positioned at the offset.

19. The computer-implemented method of claim 1, wherein determining the dwell times is based on a predetermined target dosage of radiant fluence for high-touch surfaces.

20. An article of manufacture including a non-transitory computer-readable medium, having stored thereon program instructions that, upon execution by a computing system, cause the computing system to perform operations comprising:
   obtaining a three-dimensional image map of m surfaces within an environment, wherein the surfaces are respectively associated with importance weights, and wherein the importance weights represent how frequently the surfaces are expected to be touched;
   determining a set of n vantage points for a light source within the environment;
   calculating an m×n irradiance matrix representing irradiance presented to each of the surfaces when the light source is in each of the vantage points, wherein each entry in the m×n irradiance matrix is determined by: (i) rasterizing the three-dimensional image map for a given candidate vantage point, (ii) identifying a set of visible surfaces from the three-dimensional image map as rasterized, and (iii) calculating an amount of light-based power that would reach each of the visible surfaces;
   determining a set of n dwell times, one associated with each of the vantage points, using linear programming over the m×n irradiance matrix, the importance weights, and an overall time constraint; and
   providing instructions, to a disinfecting agent, to traverse at least a subset of the vantage points, pausing at each in accordance with the associated dwell times and illuminating at least some of the surfaces while paused.

* * * * *